(12) United States Patent  
Morikawa et al.

(10) Patent No.: US 12,404,287 B2  
(45) Date of Patent: Sep. 2, 2025

(54) CHEMICAL COMPOUND, SURFACE TREATING AGENT, SURFACE TREATING METHOD, AND PRODUCTION METHOD FOR METAL-RESIN COMPOSITE

(71) Applicant: MEC COMPANY LTD., Hyogo (JP)

(72) Inventors: Koki Morikawa, Amagasaki (JP); Yuki Ogino, Amagasaki (JP); Jun Nishimine, Amagasaki (JP)

(73) Assignee: MEC COMPANY LTD., Hyogo (JP)

( * ) Notice: Subject to any disclaimer, the term of this patent is extended or adjusted under 35 U.S.C. 154(b) by 111 days.

(21) Appl. No.: 18/411,521

(22) Filed: Jan. 12, 2024

(65) Prior Publication Data  
US 2024/0270763 A1   Aug. 15, 2024

(30) Foreign Application Priority Data

Jan. 31, 2023   (JP) .................. 2023-013320

(51) Int. Cl.  
*C07F 7/18* (2006.01)  
*B32B 5/02* (2006.01)  
(Continued)

(52) U.S. Cl.  
CPC .............. *C07F 7/1804* (2013.01); *B32B 5/02* (2013.01); *B32B 7/12* (2013.01); *B32B 15/14* (2013.01);  
(Continued)

(58) Field of Classification Search  
CPC . C07F 7/1804; B32B 5/02; B32B 7/12; B32B 15/14; B32B 15/20;  
(Continued)

(56) References Cited

U.S. PATENT DOCUMENTS

2015/0152124 A1   6/2015   Mori et al.

FOREIGN PATENT DOCUMENTS

WO   2013/186941   12/2013

*Primary Examiner* — Christopher W Raimund  
(74) *Attorney, Agent, or Firm* — Wenderoth, Lind & Ponack, L.L.P.

(57) ABSTRACT

Provided is a chemical compound represented by the general formula (A), in which each of substituents $Q^1$ to $Q^6$ is bonded to a nitrogen atom of melamine backbone. In the general formula (A), at least one of $Q^1$ to $Q^6$ is X, and at least one of $Q^1$ to $Q^6$ is Y. $R^1$ is a hydrogen atom or an alkyl group having 1 to 12 carbon atoms. $R^2$ is a hydrogen atom, or a monovalent hydrocarbon group selected from the group consisting of an alkyl group having 1 to 12 carbon atoms, an aryl group having 6 to 25 carbon atoms, and an aralkyl group having 7 to 30 carbon atoms. Each of $R^{51}$ and $R^{52}$ is a divalent organic group, and a is an integer of 1 to 3.

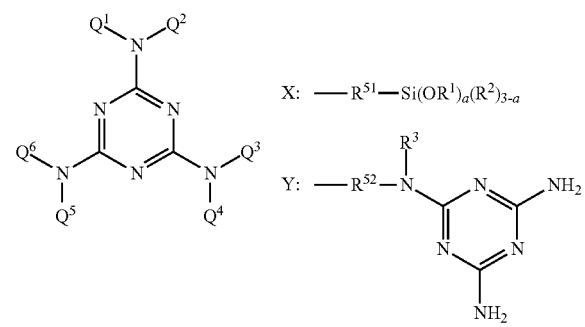

11 Claims, 1 Drawing Sheet

(51) Int. Cl.
  *B32B 7/12*    (2006.01)
  *B32B 15/14*   (2006.01)
  *B32B 15/20*   (2006.01)
  *C07D 251/54*  (2006.01)
  *C08J 5/12*    (2006.01)

(52) U.S. Cl.
  CPC ............ *B32B 15/20* (2013.01); *C07D 251/54* (2013.01); *C08J 5/12* (2013.01); *B32B 2260/021* (2013.01); *B32B 2260/046* (2013.01); *B32B 2262/101* (2013.01); *C08J 2363/00* (2013.01)

(58) Field of Classification Search
  CPC ........ B32B 2260/021; B32B 2260/046; B32B 2262/101; B32B 15/08; B32B 2311/30; C07D 251/54; C07D 251/70; C08J 5/12; C08J 2363/00; C09D 5/00; B29C 63/0004; B29C 63/0065; B29C 63/02; B29C 66/02; B29C 66/72321; B29C 66/742; C09J 4/00; C09J 183/04
  See application file for complete search history.

CHEMICAL COMPOUND, SURFACE TREATING AGENT, SURFACE TREATING METHOD, AND PRODUCTION METHOD FOR METAL-RESIN COMPOSITE

CROSS REFERENCE TO RELATED APPLICATIONS

This application claims the benefit of priority to Japanese Patent Application No. 2023-013320 filed Jan. 31, 2023, the entire contents of which are incorporated herein by reference in its entirety.

TECHNICAL FIELD

The present invention relates to a chemical compound, a surface treating agent, a surface treating method, and a production method for a metal-resin composite.

BACKGROUND ART

In the manufacture of electronic components and various molded products, a metal is adhered to a metal, a ceramic, a resin and the like, and adhesiveness between a metal and each member is required. For example, in a manufacturing process of a printed wiring board, a resin material such as an etching resist, a plating resist, a solder resist or a prepreg is adhered to a surface of a metal layer or metal wiring, and high adhesiveness is required between the metal and the resin.

A method is known in which a metal is surface-treated for enhancing adhesiveness between the metal and a resin or the like. For example, Patent Document 1 indicates that by surface-treating a metal with a chemical compound in which a Si—OH forming group (specifically, an alkoxysilyl group) is bonded to an amino group of melamine, a coating film is formed on a surface of metal to improve adhesiveness between the metal and various members.

PRIOR ART DOCUMENT

Patent Document

Patent Document 1: WO 2013/186941

SUMMARY OF THE INVENTION

Problems to be Solved by the Invention

If a metal, on which a coating film is formed by surface-treating the metal with a solution containing the chemical compound disclosed in Patent Document 1, is adhered to a resin or the like, there is a significant decrease in adhesive strength when a high accelerated stress test is conducted. An object of the present invention is to provide a chemical compound that can be suitably used as a surface treating agent for metal, and to provide a surface treating agent using the chemical compound.

Means for Solving the Problems

An aspect of the present invention is a chemical compound represented by the following general formula (A).

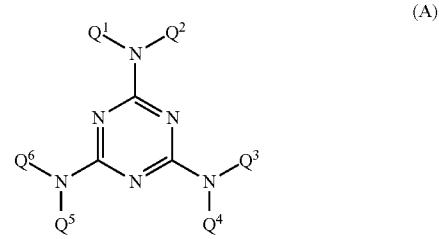

(A)

In the general formula (A), $Q^1$ to $Q^6$ are each independently a hydrogen atom, an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, X or Y. At least one of $Q^1$ to $Q^6$ is X and at least one of $Q^1$ to $Q^6$ is Y.

X: —$R^{51}$—$Si(OR^1)_a(R^2)_{3-a}$

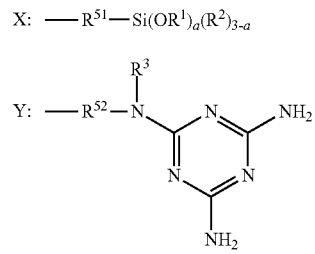

$R^{51}$ is an alkylene group having 1 to 12 carbon atoms and optionally containing a heteroatom. $R^{52}$ is an alkylene group having 1 to 12 carbon atoms and optionally containing a heteroatom; or a divalent organic group in which a main chain contains carbon and nitrogen atoms and the number of atoms forming the main chain is 20 or less and in which a part of the main chain forms a part of a 1,3,5-triazine ring, or a carbon atom of the 1,3,5-triazine ring is bonded to a nitrogen atom of the main chain. $R^1$ is a hydrogen atom or an alkyl group having 1 to 12 carbon atoms. $R^2$ is a hydrogen atom, or monovalent hydrocarbon group selected from the group consisting of an alkyl group having 1 to 12 carbon atoms, an aryl group having 6 to 25 carbon atoms, and an aralkyl group having 7 to 30 carbon atoms. a is an integer of 1 to 3. $R^3$ is a hydrogen atom, or a monovalent organic group selected from the group consisting of an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, and X.

The chemical compound of the general formula (A) can be roughly classified into chemical compounds of the following general formula (1), in which $Q^1$ is X, $Q^3$ is Y, and X and Y are bonded to different nitrogen atoms, and chemical compounds of the following general formula (2), in which $Q^1$ is X, $Q^2$ is Y, and X and Y are bonded to the same nitrogen atom.

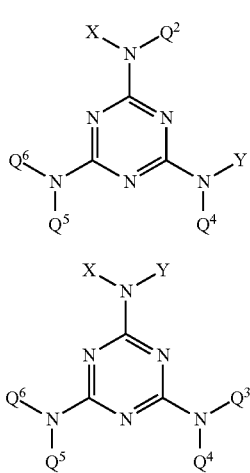

(1)

(2)

In the general formula (1), $Q^5$ may be X, Y or a hydrogen atom, and is preferably X or Y. Each of $Q^2$, $Q^4$ and $Q^6$ may be a hydrogen atom.

In the general formula (2), each of $Q^3$, $Q^4$, $Q^5$ and $Q^6$ may be a hydrogen atom.

One aspect of the present invention is a surface treating agent containing the above-described chemical compound. The surface treating agent contains the above-mentioned chemical compound and a solvent. By bringing the surface treating agent into contact with the surface of a metal member, the metal member can be surface-treated to form a coating film. The surface-treated metal member is excellent in adhesiveness to a resin. Examples of the metal member include copper and copper alloy materials.

Effects of the Invention

By surface-treating a metal member with a surface treating agent containing the above-mentioned chemical compound, adhesiveness between the metal member and a resin can be improved. By bonding the surface-treated metal member and a resin, a metal-resin composite excellent in adhesiveness at an interface between the metal member and the resin member can be obtained.

MODE FOR CARRYING OUT THE INVENTION

Chemical Structure of Compound

Figure 1:
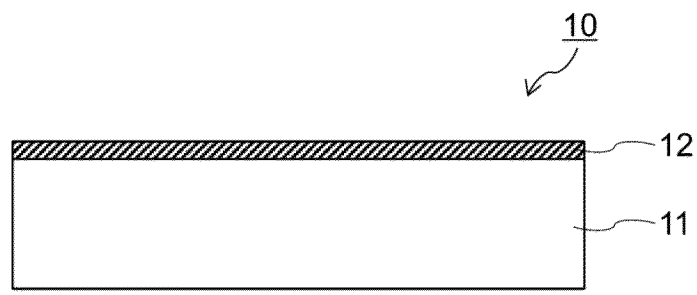
FIG. 1 is a schematic cross-sectional view showing one embodiment of a surface-treated metal member.

A chemical compound of the present invention is a melamine derivative represented by the following general formula (A). Melamine is a chemical compound having amino groups (—$NH_2$) at the 2-, 4-, and 6-positions of a 1,3,5-triazine ring, and a melamine derivative is obtained by substituting the hydrogen atom of the amino group.

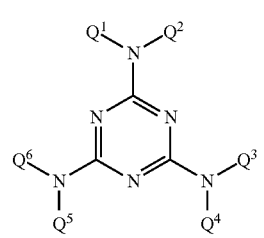

(A)

$Q^1$ to $Q^6$ in the general formula (A) are each independently a hydrogen atom, an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, X or Y.

X:  —$R^{51}$—$Si(OR^1)_a(R^2)_{3-a}$

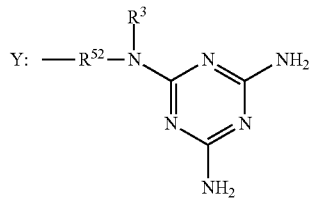

In X and Y, each of $R^{51}$ and $R^{52}$ is a divalent organic group. In X, $R^1$ is a hydrogen atom or an alkyl group having 1 to 12 carbon atoms. $R^2$ is a hydrogen atom, or monovalent hydrocarbon group selected from the group consisting of an alkyl group having 1 to 12 carbon atoms, an aryl group having 6 to 25 carbon atoms, and an aralkyl group having 7 to 30 carbon atoms. a is an integer of 1 to 3.

In Y, $R^3$ is a hydrogen atom, or a monovalent organic group selected from the group consisting of an amino group, an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, and X.

The chemical compound of the present invention is characterized in that at least one of the of the substituents $Q^1$ to $Q^6$ is X and at least one of the substituents $Q^1$ to $Q^6$ is Y, wherein each of substituents $Q^1$ to $Q^6$ in the general formula (A) is a substituent bonded to nitrogen atom. Due to the presence of X and Y in the same molecule, coating film formability on a surface of a metal or the like is improved, and degradation of the coating film formed from the above-mentioned chemical compound tends to be suppressed even in a high-temperature and high-humidity environment.

In the chemical compound represented by the general formula (A) (hereinafter, sometimes referred to as "compound (A)"), two or more of $Q^1$ to $Q^6$ may be X and two or more of $Q^1$ to $Q^6$ may be Y. Two or more X groups may be the same or different. Two or more Y groups may be the same or different. In the compound (A), X and Y may be bonded to the same nitrogen atom, or X and Y may be bonded to different nitrogen atoms.

X is a group having an alkoxysilyl group and/or a silanol group at an end thereof. —Si—$OR^1$ is a silanol group when $R^1$ is a hydrogen atom, whereas —Si—$OR^1$ is an alkoxysilyl group when $R^1$ is an alkyl group. The alkoxysilyl group forms a silanol group through hydrolysis. From the viewpoint of stability of the chemical compound, $R^1$ is preferably an alkyl group. From the viewpoint of coating film formability and improvement of adhesive strength, a is preferably two or more, particularly preferably 3. That is, —Si(OR$^1$)$_a$ (R$^2$)$_{3-a}$ in X is preferably a dialkoxymonoalkylsilyl group or a trialkoxysilyl group, particularly preferably a trialkoxysilyl group.

When $R^1$ is an alkyl group, —Si—OR$^1$ of X is hydrolyzed to form a silanol group, and the chemical compound represented by the general formula (A) is condensed by condensation of silanol to form a coating film. From the viewpoint of excellent hydrolyzability, $R^1$ is preferably an alkyl group having 6 or less carbon atoms. Examples of the alkyl group having 6 or less carbon atoms include a methyl group, an ethyl group, a propyl group, an isopropyl group, a butyl group, an isobutyl group, a tert-butyl group, a pentyl group, and a hexyl group. Among them, a methyl group or an ethyl group is preferable.

When a in X is 1 or 2, $R^2$ is preferably a hydrogen atom or an alkyl group having 1 to 6 carbon atoms. Specific examples of the alkyl group having 1 to 6 carbon atoms are as described above. Among them, a methyl group or an ethyl group is preferable.

Y has an amino group (—NH$_2$) directly bonded to a carbon atom of the 1,3,5-triazine ring. Due to the presence of two amino groups directly bonded to a carbon atom of the 1,3,5-triazine ring, the coating film formed from the compound (A) contributes to the improvement of adhesiveness between members, and degradation of the coating film in a high-temperature and high-humidity environment tends to be suppressed, leading to maintenance of high adhesiveness.

Due to its chemical structure, the compound (A) inherently has a molecular weight of 380 or more. The molecular weight of the compound (A) may be 400 or more or 420 or more. If the molecular weight of the compound (A) is excessively large, solubility in a solvent and coating film formability tend to be deteriorated. Therefore, the molecular weight of the compound (A) is preferably 2,000 or less, more preferably 1,500 or less, and may be 1,200 or less or 1,000 or less.

The compound (A) having at least one X group and at least one Y group is roughly classified into chemical compounds in which X and Y are bonded to different nitrogen atoms (sometimes referred to as "compound (1)") and chemical compounds in which X and Y are bonded to the same nitrogen atom (sometimes referred to as "compound (2)").

Compound (1)

A chemical compound of the general formula (A) in which X and Y are bonded to different nitrogen atoms is represented by the following general formula (1).

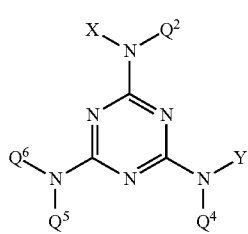

(1)

In the general formula (1), $Q^2$, $Q^4$, $Q^5$ and $Q^6$ are each independently a hydrogen atom, an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, X or Y.

In the general formula (1), $Q^5$ is preferably X or Y. That is, the compound (1) is preferably a chemical compound represented by the following general formula (11) or (12).

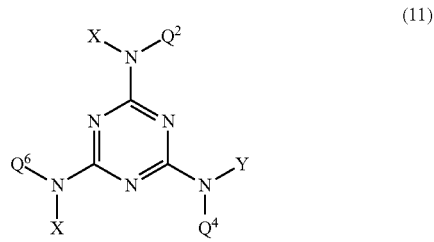

(11)

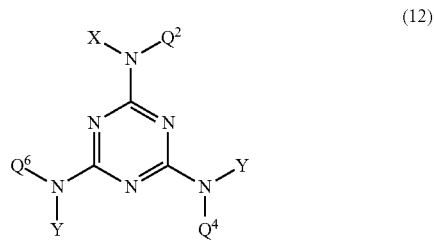

(12)

In the general formulae (11) and (12), $Q^2$ is preferably a hydrogen atom or X. $Q^4$ and $Q^6$ are each independently a hydrogen atom, an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, or X. Each of $Q^4$ and $Q^6$ is preferably a hydrogen atom, or X.

A chemical compound of general formula (11) or (12) in which $Q^2$ is X or a hydrogen atom and each of $Q^4$ and $Q^6$ is a hydrogen atom is represented by any of the following general formulae.

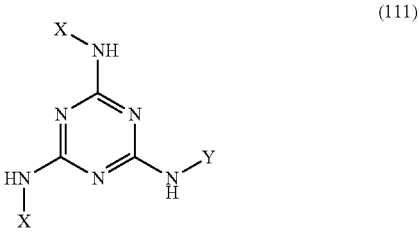

(111)

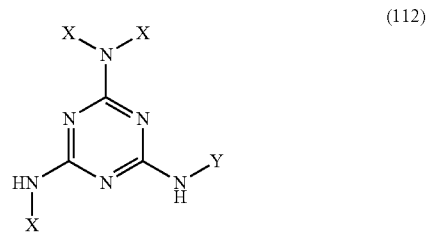

(112)

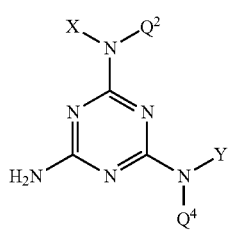

(121)

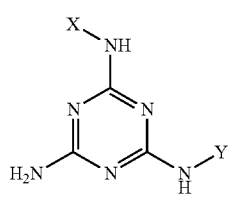

(122)

In the general formula (1), each of $Q^5$ and $Q^6$ may be a hydrogen atom. A chemical compound of the general formula (1) in which each of $Q^5$ and $Q^6$ is a hydrogen atom is represented by the following general formula (13).

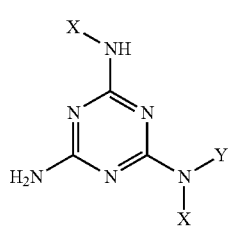

(13)

In the general formula (13), $Q^2$ is preferably a hydrogen atom or X, and $Q^4$ is preferably a hydrogen atom or X. A chemical compound of the general formula (13) in which $Q^2$ is X or a hydrogen atom and $Q^4$ is a hydrogen atom or X can be represented by any of the following general formulae.

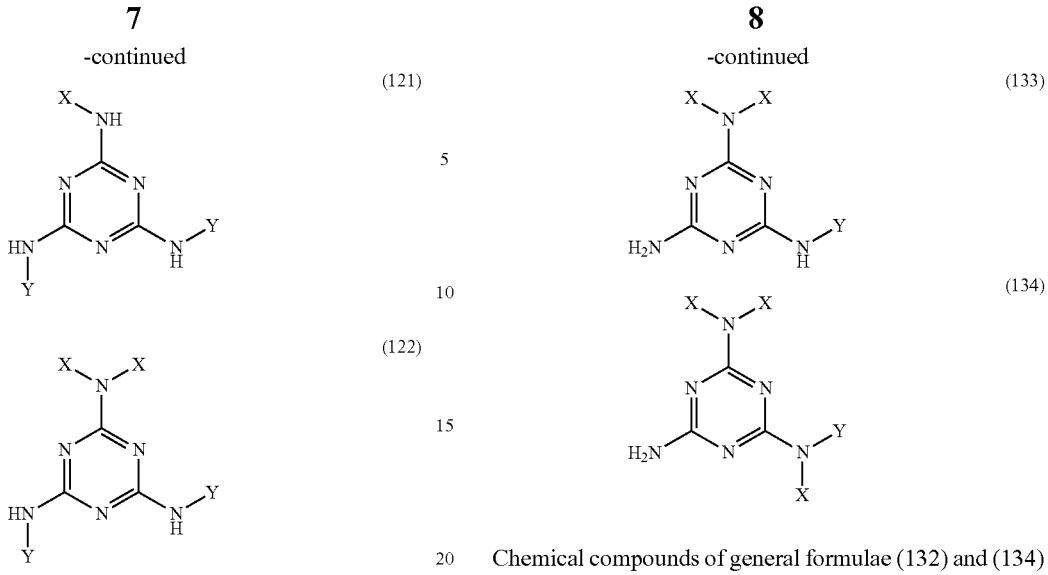

(131)

(132)

(133)

(134)

Chemical compounds of general formulae (132) and (134) correspond to the compound (1) because $Q^1$ is X and $Q^3$ is Y, and X and Y are bonded to different nitrogen atoms in the general formula (A). Chemical compounds of general formulae (132) and (134) also correspond to the compound (2) because $Q^3$ is Y and $Q^4$ is X, and X and Y are bonded to the nitrogen atom in the general formula (A).

From the viewpoint of coating film formability on a metal surface, interlayer adhesion and coating film durability, the compound (1) is preferably one in which each of the numbers of X groups and Y groups is 1 or 2, and one or both of the numbers of X groups and Y groups are 2. Among the structures described above, those of general Formulae (111), (121), (122) and (133) are preferable.

$R^{51}$ in X, which is a linking group connecting a nitrogen atom of an amino group of melamine and a silicon atom of a silyl group, is an alkylene group having 1 to 12 carbon atoms and optionally containing a heteroatom. When the compound (1) contains two or more X groups, $R^{51}$ groups in the respective X groups may be the same or different.

$R^{51}$ may be linear or branched. The number of atoms forming the main chain of $R^{51}$ (the number of atoms between the nitrogen atom of the amino group of melamine and the silicon atom of the silyl group) is preferably 1 to 12, more preferably 2 to 12.

$R^{51}$ may be an alkylene group or a heteroalkylene group containing an atom other than carbon (i.e., a heteroatom) in the main chain. The heteroalkylene group may contain an ether bond, a thioether bond, an ester bond, an amide bond, a carbonyl group, an amino group, an imino group, or the like. $R^{51}$ is preferably a linear alkylene group or heteroalkylene group having 1 to 12 carbon atoms. Among them, a linear alkylene group having 1 to 12 carbon atoms is preferable. When $R^{51}$ is a linear alkylene group, the number of carbon atoms is preferably 1 to 8, more preferably 2 to 6. $R^{51}$ may be propylene. Specific examples of the branched alkylene group include an isopropylene group, an isobutylene group, and an isopentene group.

$R^3$ in Y is a hydrogen atom, an amino group, an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, or X. In particular, $R^3$ is preferably a hydrogen atom. $R^3$ other than a hydrogen atom is preferably an alkyl group having 1 to 6 carbon atoms, a phenyl group, a benzyl group, an amino group, X, or the like.

$R^{52}$ in Y, which is a linking group connecting nitrogen atoms of amino groups of two adjacent melamine backbones, is a divalent organic group. When the compound (1) contains two or more Y groups, $R^{52}$ groups in the respective Y groups may be the same or different.

$R^{52}$ may be linear or branched. $R^{52}$ may contain a ring structure. The number of atoms forming the main chain of $R^{52}$ (i.e., the number of atoms between the nitrogen atoms of the amino groups of two melamine backbones) is preferably 1 to 20.

$R^{52}$ is, for example, an alkylene group having 1 to 12 carbon atoms and optionally containing a heteroatom. The alkylene group having 1 to 12 carbon atoms and optionally containing a heteroatom may be an alkylene group or a heteroalkylene group containing an atom other than carbon (a heteroatom) in the main chain. The heteroalkylene group may contain an ether bond, a thioether bond, an ester bond, an amide bond, a carbonyl group, an amino group, an imino group, or the like. $R^{52}$ may be a linear alkylene group or heteroalkylene group having 1 to 12 carbon atoms. When the heteroalkylene contains a nitrogen atom (amino group) in the main chain, $R^{52}$ may contain a branched structure in which an alkyl group is bonded to the nitrogen atom of the heteroalkylene.

As described above, $R^{52}$ may contain a ring structure. Examples of $R^{52}$ containing a ring structure include divalent organic groups in which the number of atoms forming the main chain is 20 or less, and the atoms forming the main chain form a part of the ring structure, and divalent organic groups in which a ring structure outside the main chain is bonded to a nitrogen atom of the main chain. The ring structure is preferably a 1,3,5-triazine ring.

Examples of $R^{52}$ in which atoms forming the main chain form a part of the ring structure include those containing a melamine backbone, and a part of the main chain forms a part of a 1,3,5-triazine ring. Examples of such a chemical compound having $R^{52}$ include chemical compounds represented by the following general formula (125).

$R^3$, $Q^2$, $Q^4$, $Q^6$ and X in the general formula (125) are the same as $R^3$, $Q^2$, $Q^4$, $Q^6$ and X described above, and a plurality of $R^3$, $Q^2$, $Q^4$, $Q^6$ and X groups may be the same or different. Each of $R^3$, $Q^2$, $Q^4$ and $Q^6$ is preferably a hydrogen atom.

The structure of the general formula (125) is an example of the structure of the general formula (12), and $Y^1$ and $Y^2$ correspond to two Y groups in the general formula (12). In $Y^1$, an ethylene group $R^{521}$ surrounded by a broken line corresponds to the divalent organic group $R^{52}$ in Y. In $Y^2$, $R^{522}$ surrounded by a broken line corresponds to the divalent organic group $R^{52}$ in Y. In $R^{522}$, —C—C—N—[C=N—C]—N—C—C— constitutes a main chain, and the [C=N—C] part is a constituent of a 1,3,5-triazine ring.

The structure of the general formula (125) has been described as an example in which atoms forming the main chain of the divalent organic group $R^{52}$ of Y form a part of the ring structure, but the example in which atoms forming the main chain of $R^{52}$ form a part of the ring structure is not limited thereto. For example, $R^{52}$ may contain two or more ring structures, or may contain a structure in which two or more melamine backbones are linked. When $R^{52}$ contains a melamine backbone, it is not necessarily required that X be bonded to a nitrogen atom of melamine of $R^{52}$. For example, instead of X of $R^{522}$ in the general formula (125), a hydrogen atom, an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, or the like may be bonded to a nitrogen atom of melamine.

Examples of $R^{52}$ in which the ring structure outside the main chain is bonded to a nitrogen atom of the main chain include those in which a carbon atom of a 1,3,5-triazine ring is bonded to a nitrogen atom of the main chain. Examples of such a chemical compound having $R^{52}$ include chemical compounds represented by the following general formula (135).

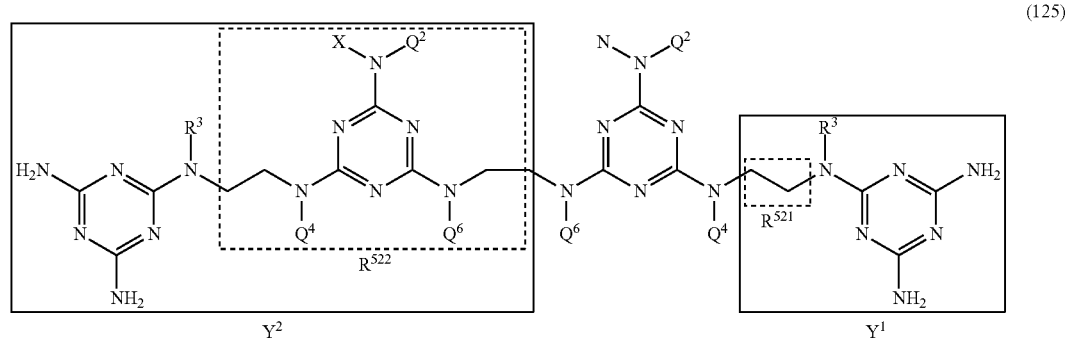

(125)

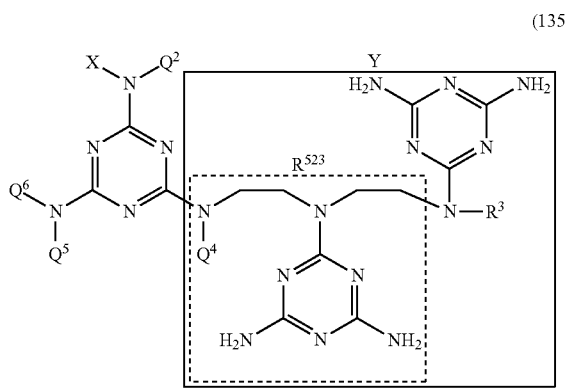

(135)

$R^3$, $Q^2$, $Q^4$, $Q^5$, $Q^6$ and X in the general formula (135) are the same as $R^3$, $Q^2$, $Q^4$, $Q^5$, $Q^6$ and X described above. $R^3$ is preferably a hydrogen atom. Each of $Q^2$, $Q^4$, $Q^5$ and $Q^6$ is preferably a hydrogen atom, X or Y.

Y in the general formula (135) corresponds to Y in the general formula (1), and the $R^{523}$ part surrounded by a broken line corresponds to a divalent organic group $R^{52}$ in Y. In $R^{523}$, —C—C—N—C—C-forms a main chain, and a nitrogen atom of the main chain is bonded to a carbon atom of a 1,3,5-triazine ring to form a part of a melamine backbone.

The structure of the general formula (135) has been described as an example of a chemical compound in which the divalent organic group $R^{52}$ of Y has a ring structure outside the main chain, but the chemical compound in which $R^{52}$ has a ring structure outside the main chain is not limited thereto. For example, $R^{52}$ may be one in which a main chain and a ring structure outside the main chain are indirectly bonded and a divalent organic group such as an alkylene group is interposed therebetween. $R^{52}$ may have two or more ring structures outside the main chain, or may contain two or more melamine backbones. When $R^{52}$ contains a melamine backbone, a constituent other than a hydrogen atom may be bonded to a nitrogen atom that is not involved in bonding to the main chain (an exocyclic nitrogen atom bonded to carbon atoms at the 4- and 6-positions of the triazine ring in the general formula (135)). For example, one or both of two hydrogen atoms in each of two —NH$_2$ groups present in $R^{523}$ in the general formula (135) may be independently substituted with an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, X, Y, or the like.

Compound (2)

A chemical compound of the general formula (A) in which X and Y are bonded to the same nitrogen atom is represented by the following general formula (2).

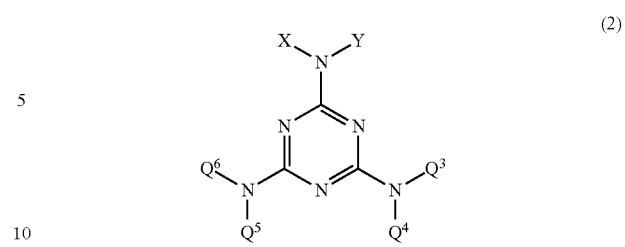

(2)

In the general formula (2), $Q^3$, $Q^4$, $Q^5$ and $Q^6$ are each independently a hydrogen atom, an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, X or Y. Details of X and Y are as described above for the compound (1).

In the general formula (2), each of $Q^3$, $Q^4$, $Q^5$ and $Q^6$ is preferably a hydrogen atom. That is, the compound (2) is preferably a chemical compound of the following formula (21).

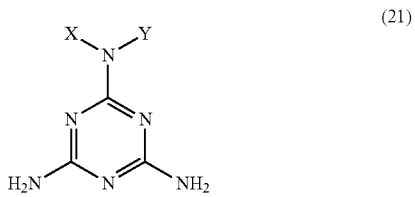

(21)

X and Y in the general formula (21) are rewritten to the specific forms to obtain the following general formula (22).

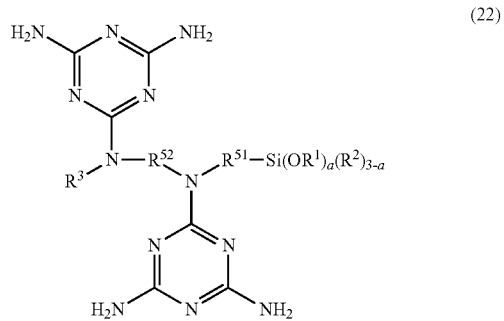

(22)

Details of $R^1$, $R^2$, a, $R^3$, $R^{51}$ and $R^{52}$ in the general formula (22) are as described above.

As described above in detail for the compound (1), $R^{52}$ is a linking group connecting nitrogen atoms of amino groups of two adjacent melamine backbones, preferably an alkylene group having 1 to 12 carbon atoms and optionally containing a heteroatom; or a divalent organic group in which a main chain contains carbon and nitrogen atoms and the number of atoms forming the main chain is 20 or less and in which a part of the main chain forms a part of a ring structure, or a ring structure outside the main chain is bonded to a nitrogen atom of the main chain. $R^{52}$ is typically a linear alkylene, and specific examples thereof include an ethylene group, a propylene group, a butene group, a pentene group, and a hexene group. $R^{52}$ may be a heteroalkylene group. When $R^{52}$ has a ring structure, the ring structure is preferably a 1,3,5-triazine ring.

Examples of the chemical compound of the general formula (22) in which $R^{52}$ contains a ring structure outside the main chain include those in which a carbon atom of a 1,3,5-triazine ring is bonded to a nitrogen atom of the main chain of $R^{52}$. Examples of such a chemical compound having $R^{52}$ include ones represented by the following general formula (225).

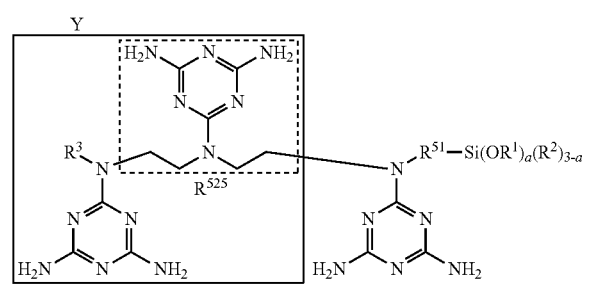

(225)

$R^1$, $R^2$, a, $R^3$ and $R^{51}$ in the general formula (225) are as described above. Y in the general formula (225) corresponds to Y in the general formula (21), and the $R^{525}$ part surrounded by a broken line corresponds to a divalent organic group $R^{52}$ in Y. In $R^{525}$, —C—C—N—C—C— forms a main chain, and a nitrogen atom of the main chain is bonded to a carbon atom of a 1,3,5-triazine ring to form a part of a melamine backbone.

The structure of the general formula (225) has been described as an example of a chemical compound in which the divalent organic group $R^{52}$ of Y has a ring structure outside the main chain, but the chemical compound in which $R^{52}$ has a ring structure outside the main chain is not limited thereto, and may contain various chemical structures as described above for the compound (1).

As described in detail above for the compound (1), $R^3$ is a hydrogen atom, an amino group, an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, or X. In particular, $R^3$ is preferably a hydrogen atom. $R^3$ other than a hydrogen atom is preferably an alkyl group having 1 to 6 carbon atoms, a phenyl group, a benzyl group, an amino group, X, or the like. Specific examples of the chemical compound in which $R^3$ in the general formula (22) is X include, but are not limited to, Compound 21 in EXAMPLES described later.

Method for Synthesizing Chemical Compound

The methods for synthesizing the chemical compounds described above are not limited. From the viewpoint of the high reactivity and yield, and the like, a method using a reaction of a chlorine atom of a 1,3,5-triazine derivative in which a chlorine atom is bonded to one or more of carbon atoms at the 2-, 4- and 6-positions of 1,3,5-triazine is preferable. The reaction (dehydrochlorination condensation) between the chlorine atom bonded to the carbon atom of the 1,3,5-triazine ring and an amino group gives a chemical compound in which a nitrogen atom is bonded to a carbon atom of a triazine ring.

Synthesis of Compound (1)

As shown in the Scheme 1 below, chemical compound of the general formula (121) which has one X group and two Y groups can be obtained by a reaction between 1,3,5-triazine derivative (61) and melamine derivative (71), wherein the 1,3,5-triazine derivative (61) has —NH—$R^{51}$—Si(OR$^1$)$_a$(R$^2$)$_{3-a}$ and a chlorine atom as substituents on the carbon atom, and the melamine derivative (71) is one in which a hydrogen atom of an amino group of melamine is substituted with an aminoalkyl group —$R^{52}$—NH$_2$.

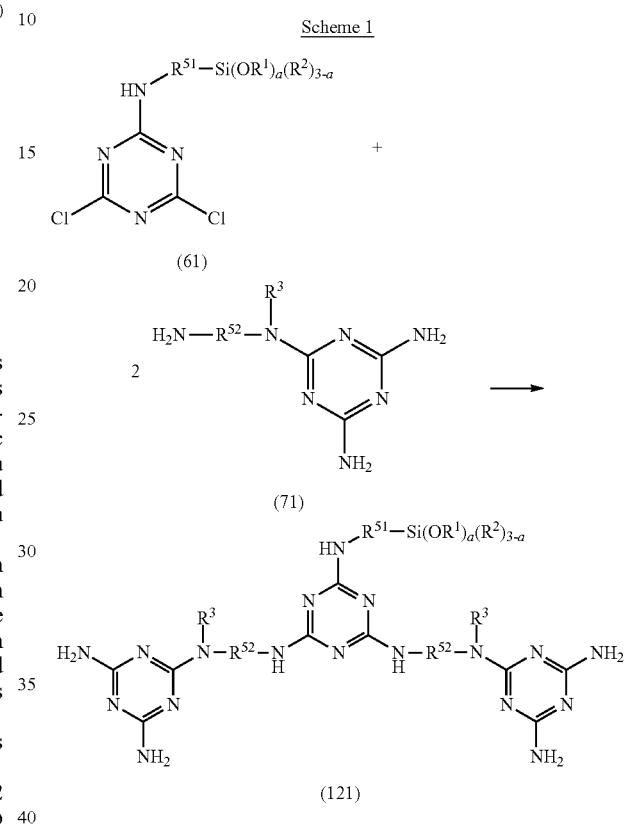

Scheme 1

As shown in the Scheme 2 below, chemical compound of the general formula (111) which has two X groups and one Y group can be obtained by a reaction between the 1,3,5-triazine derivative (62) and the melamine derivative (71).

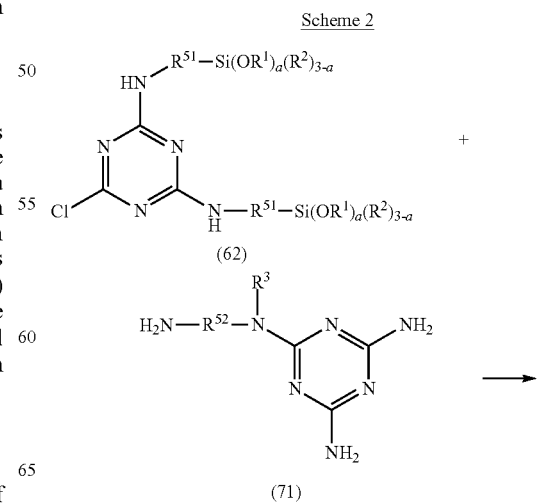

Scheme 2

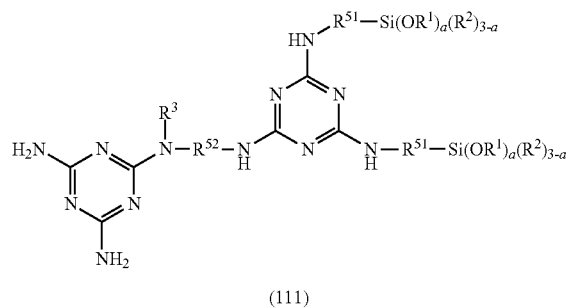

(111)

As shown in the Scheme 3 below, chemical compound of the general formula (122) which has two X groups and two Y groups can be obtained by using 1,3,5-triazine derivative (63) having —N[R$^{51}$—Si(OR$^1$)$_a$(R$^2$)$_{3-a}$]$_2$ and a chlorine atom as substituents instead of the 1,3,5-triazine derivative (61) in the Scheme 1.

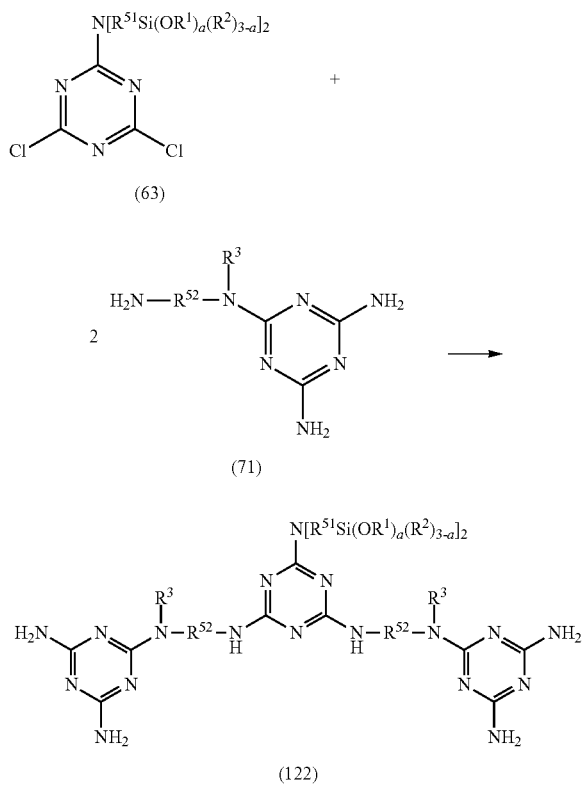

Chemical compound of the general formula (125) can be obtained by using the following 1,3,5-triazine derivative (64) instead of the 1,3,5-triazine derivative (61) in the Scheme 1.

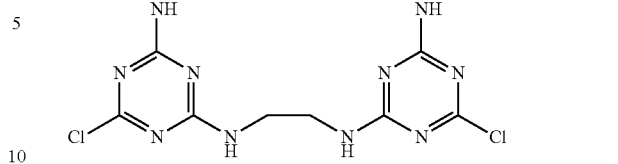

The reaction between each of the 1,3,5-triazine derivatives (61) to (64) and the melamine derivative (71) is carried out, for example, at a temperature of about 20 to 200° C. in the presence of a base.

The 1,3,5-triazine derivatives (61) to (63) having a hydrolyzable silyl group and a chlorine atom as substituents can be synthesized by the method disclosed in WO 2013/186941. Specifically, chemical compounds (61) and (62) can be obtained by the reaction between cyanuric chloride and an aminosilane compound such as 3-aminopropyltrimethoxysilane or 3-aminopropyltriethoxysilane. Chemical compound (63) can be obtained by a reaction between cyanuric chloride and an aminosilane compound such as bis[3-(trimethoxysilyl)propyl]amine or bis[3-(triethoxysilyl)propyl]amine.

Chemical compound (64) can be synthesized by a reaction between the chemical compound (61) and ethylenediamine as shown in the Scheme 4 below. In this reaction, generation of trimers and higher multimers can be suppressed when the amount of the chemical compound (61) is larger than two times that of ethylene diamine in terms of a molar number.

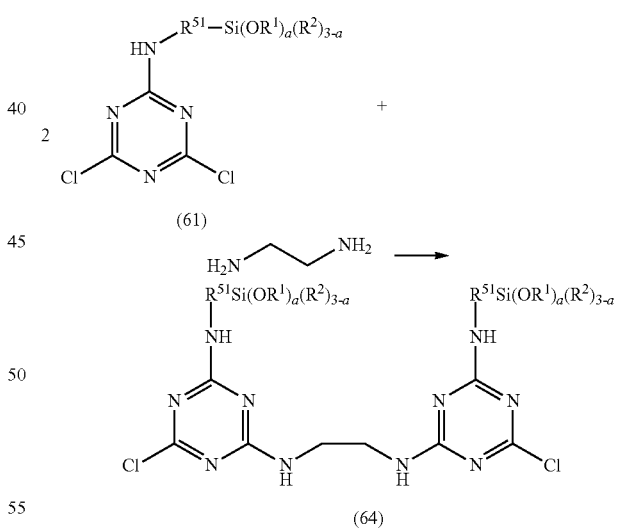

The chain length between the nitrogen atoms of two adjacent melamine backbones can be changed by using diamines having different chain lengths, such as diaminopropane, diaminobutane, diaminopentane and hexamethylenediamine instead of ethylenediamine.

A melamine derivative in which a hydrogen atom of the amino group of melamine is substituted with an aminoalkyl group —R$^{52}$—NH$_2$ can be obtained by, for example, a reaction between 2-chloro-4,6-diamino-1,3,5-triazine and a diamine (H$_2$N—R$^{52}$—NH$_2$) as shown in the Scheme 5 below. In this reaction, generation of multimers can be suppressed when the amount of the diamine is larger than that of 2-chloro-4,6-diamino-1,3,5-triazine.

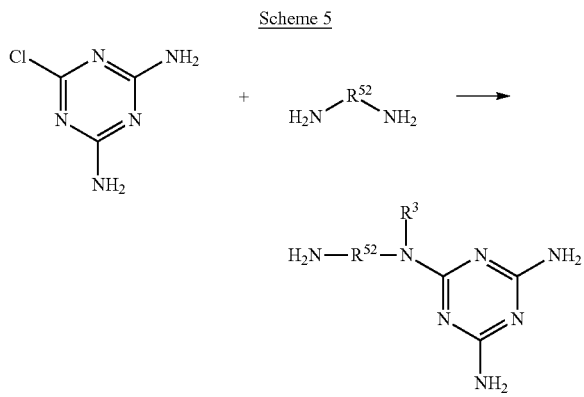

Synthesis of Compound (2)

As shown in the Scheme 6 below, a chemical compound of the general formula (22), in which X and Y are bonded to the same nitrogen atom, can be obtained by a reaction between 2-chloro-4,6-diamino-1,3,5-triazine and an aminosilane compound (81).

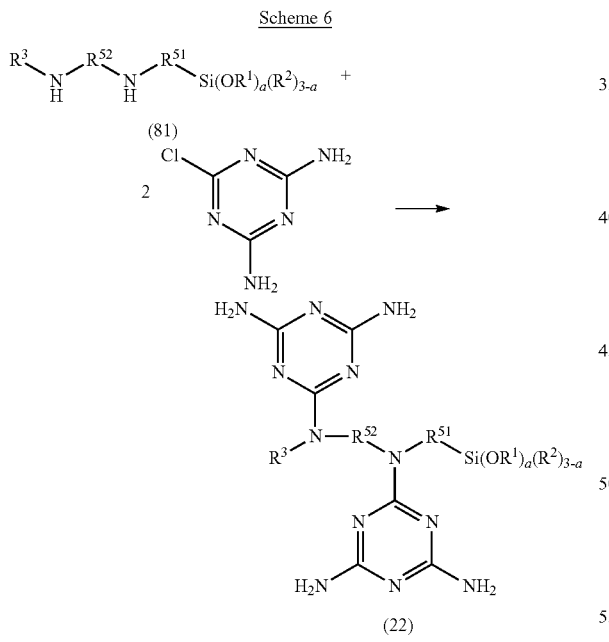

From the viewpoint of increasing the reaction yield, it is preferable that the amount of 2-chloro-4,6-diamino-1,3,5-triazine is larger than two times that of the aminosilane compound (81) in terms of a molar number in the reaction of the Scheme 6. When $R^3$ is a hydrogen atom, the aminosilane compound (81) hardly reacts with 2-chloro-4,6-diamino-1,3,5-triazine. This is because when one of the two hydrogen atoms of the primary amino group (—NH$_2$) at an end undergoes dehydrochlorination condensation with 2-chloro-4,6-diamino-1,3,5-triazine, the other hydrogen atom of the amino group has low acidity, and is inhibited from reacting by steric hindrance or the like. For this reason, little side-reaction product is generated despite an excessive amount of 2-chloro-4,6-diamino-1,3,5-triazine.

Specific examples of the aminosilane compound (81) in which $R^3$ is a hydrogen atom include 3-(2-aminoethylamino)propyltrimethoxysilane, 3-(2-aminoethylamino)propyltriethoxysilane, 3-(2-aminoethylamino)propyldimethoxymethylsilane, 3-(6-aminohexylamino)propyltrimethoxysilane, 3-(6-aminohexylamino)propyltriethoxysilane, 8-(2-aminoethylamino)octyltrimethoxysilane, 8-(2-aminoethylamino)octyltriethoxysilane, 3-(2-aminoethylamino)isobutyltrimethoxysilane, and 3-(2-aminoethylamino)isobutyltriethoxysilane.

$R^3$ in the aminosilane compound (81) is not limited to a hydrogen atom, and may be an alkyl group having 1 to 6 carbon atoms, a phenyl group, a benzyl group, or the like, and $R^3$ may contain a hydrolyzable silyl group. Specific examples of the aminosilane compound (81) in which $R^3$ contains a hydrolyzable silyl group include N,N'-bis[3-(trimethoxysilyl)propyl]ethane-1,2-diamine.

As the aminosilane compound, one having two or more of —NH— groups between the hydrolyzable silyl group and the amino group (—NHR$^3$) at an end may be used. For example, as shown in the Scheme 7 below, chemical compound of the general formula (225) can be obtained by a reaction between aminosilane compound (82) having two or more of —NH— groups and 2-chloro-4,6-diamino-1,3,5-triazine.

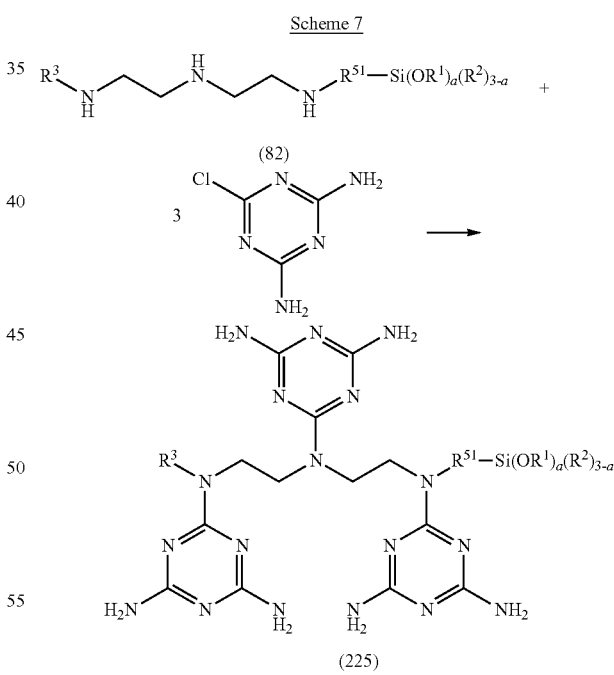

Specific examples of the aminosilane compound (82) include 3-[2-(2-aminoethylamino)ethylamino]propyltrimethoxysilane, and 3-[2-(2-aminoethylamino)ethylamino]propyltriethoxysilane.

The reaction between each of the aminosilane compounds (81) and (82) and 2-chloro-4,6-diamino-1,3,5-triazine is carried out, for example, at a temperature of about 20 to 200° C. in the presence of a base.

[Surface Treating Agent]

The compound (A) may be used as a surface treating agent for metal members and resin members. For example, by dissolving the compound (A) in a solvent, a surface treating agent is prepared. The solvent is not limited as long as it can dissolve the compound (A), and water, dimethyl sulfoxide, alcohols such as ethanol and isopropyl alcohol, amides such as N-methyl-2-pyrrolidone and N,N-dimethylformamide, esters, ethers, cellosolves such as butyl cellosolve, ketones, aromatic hydrocarbons, and the like may be used. The solvent may be a mixed solvent. As the water, one free of ionic substances and impurities is preferable, and for example, deionized water, pure water, ultrapure water and the like are preferably used.

The concentration of the compound (A) in the surface treating agent is not limited, and is preferably about 0.01 to 60 wt % from the viewpoint of achieving both coating film formability on a metal surface and solution stability. The concentration of the compound (A) in the surface treating agent may be 0.05 to 50 wt %, 0.1 to 30 wt %, 0.5 to 25 wt %, or 1 to 20 wt %. The molar concentration of the compound (A) in the surface treating agent is, for example, about 0.1 to 1,500 mmol/L, and may be 1 to 1,000 mmol/L, 5 to 500 mmol/L, or 10 to 300 mmol/L.

The surface treating agent may contain two or more kinds of compound (A). When two or more kinds of compound (A) are contained, the total concentration is preferably in the above-described range.

The surface treating agent may contain various additives in addition to the compound (A) and the solvent. Examples of the additives include metal ions such as copper ions or salts thereof, complexing agents, surfactants, stabilizers, silane coupling agents, and pH adjusters.

[Surface Treatment of Metal Member]

The above surface treating agent is brought into contact with a surface of a metal member, and the solvent is removed by drying as necessary. As a result, as shown in FIG. 1, a coating film 12 is formed on a surface of the metal member 11. When the coating film 12 formed from the compound (A) is disposed on a surface of the metal member 11, adhesiveness between the metal member and a resin improves.

The coating film 12 is formed by adsorption of the compound (A) to a metal surface. The compound (A) has at least four primary amino groups (—NH$_2$) directly bonded to the carbon atoms of the 1,3,5-triazine ring, and the primary amino groups are likely to be coordinated to the metal. Since the —Si—OR$^1$ group of the compound (A) has a hydrolytic condensation property, the compound (A) adsorbed to the metal surface can form a covalent bond between the molecules. Thus, the compound (A) may be excellent in coating film formability on a metal surface, and unlikely to cause degradation of the coating film in a high-temperature and high-humidity environment, and contribute to improvement of adhesiveness between members.

Examples of metal members include the surface of a copper foil (electrolytic copper foil, rolled copper foil) used for electronic components such as semiconductor wafers, electronic substrates, and leadframes, decorative items, building materials, and the like, the surface of a copper-plated film (electroless copper-plated film, electrolytic copper-plated film), and also wire-shaped, rod-shaped, tube-shaped, and plate-shaped copper materials for various applications. In particular, the above-mentioned surface treating agent has excellent coating film formability on a copper or copper alloy surface. Therefore, as the metal member, it is preferable to use a copper foil, a copper-plated film, a copper material, or the like. The surface of the metal member may be flat or roughened. By forming a coating film on a surface of a roughened metal member, adhesion between the metal member and the resin can be further improved.

The surface treatment of a metal member may be performed under conditions exemplified below.

In general, the surface of the metal member is washed with an acid or the like. In addition to washing, corona discharge treatment, plasma discharge treatment, ultraviolet irradiation, acid treatment, alkali treatment, water vapor treatment, and the like may be performed. Next, the surface treating agent is brought into contact with the metal member. For example, the metal member is immersed in the above-described treatment liquid, and immersed for about 2 seconds to 30 minutes. The temperature of the solution is preferably about 10 to 50° C., more preferably about 15 to 35° C. In the immersion treatment, shaking may be performed if necessary. As a method for bringing the surface treating agent into contact with the metal member, a coating method such as a spraying method, a bar coating method, a spin coating method, a comma coating method or an inkjet method may be adopted as well as an immersion method. After the surface treating agent is brought into contact with the metal member, an excess solution deposited on the metal surface is removed to obtain a surface-treated metal member 10 having the coating film 12 on the metal member 11.

Examples of the method for removing an excess solution deposited on the metal surface include drying and rinsing. In general, water or an aqueous solution is used for washing off an excess surface treating agent in the form of a solution deposited on the metal surface. A dilute acid or an aqueous alkali solution may be used as the rinsing solution. As the dilute acid, for example, sulfuric acid or hydrochloric acid at about 0.1 to 6 wt % is used. As the alkali, an aqueous NaOH solution or an aqueous KOH solution at about 0.1 to 5 wt % is used. An organic solvent may be used as the rinsing solution.

Although the coating film 12 is formed only on one side of the plate-shaped metal member 11 in FIG. 1, the coating film may also be formed on both sides of a metal member by surface-treating both sides of the metal member. It is preferable that the coating film is formed over the entire surface joined to a resin. The method for forming a coating film on a surface of a metal member is not limited to the immersion method, and it is possible to select a suitable application method such as spraying or bar coating.

[Metal-Resin Composite]

Figure 2:
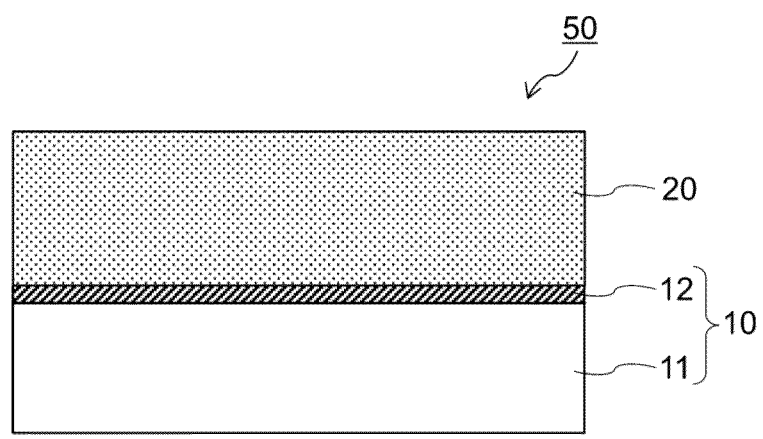
FIG. 2 is a schematic cross-sectional view showing one embodiment of a metal-resin composite.

Onto the coating film 12-formed surface of the surface-treated metal member 10, a resin member 20 is joined, whereby a metal-resin composite 50 shown in FIG. 2 is obtained.

Although the resin member (resin layer) 20 is stacked only on one side of the plate-shaped metal member 11 with the coating film 12 therebetween in FIG. 2, the resin member may also be joined on both sides of a metal member.

Before deposition of the resin member on the coating film, treatment for improvement of the wettability of the coating film surface or treatment suitable for the storage environment may be performed. Examples of the treatment of the coating film surface include washing treatment, corona discharge treatment, plasma discharge treatment, ultraviolet irradiation, acid treatment, alkali treatment, and water vapor treatment. Treatment such as heating may be performed before deposition of the resin member on the coating film. A coating film formed from the surface treating agent containing the compound (A) is hardly degraded by heating, and therefore can exhibit high adhesiveness between the metal and the resin even when heating is performed before deposition of the resin member or during deposition of the resin member.

As the method for joining the surface-treated metal member 10 and the resin member 20 together, it is possible to employ a method such as lamination pressing, lamination, coating, injection molding, or transfer molding. After deposition of the resin layer, the resin may be cured by heating or active ray irradiation.

The resin constituting the above resin member is not particularly limited, and examples thereof include thermoplastic resins such as acrylonitrile/styrene copolymer resin (AS resin), acrylonitrile/butadiene/styrene copolymer resin (ABS resin), fluorine resin, polyamide, polyethylene, polyethylene terephthalate, polyvinylidene chloride, polyvinyl chloride, polycarbonate, polystyrene, polysulfone, polypropylene, and liquid crystal polymer, thermosetting resins such as epoxy resin, phenol resin, polyimide, polyurethane, bis-maleimide-triazine resin, modified polyphenylene ether, and cyanate ester, and UV-curable resins such as UV-curable epoxy resin and UV-curable acrylic resin. These resins may be modified with a functional group or may also be reinforced with, for example, glass fibers, aramid fibers, or other fiber.

The coating film formed on a metal surface using the surface treating agent containing the compound (A) exhibits excellent adhesiveness between metal and resin. Therefore, without additional layers therebetween, the resin member 20 can be directly joined onto the coating film 12 disposed on the metal member surface. In other words, when the surface treating agent containing the compound (A) is used, without additional treatments, a metal-resin composite having high adhesiveness can be obtained by simply forming a coating film on a metal member surface, and joining a resin member directly thereonto.

EXAMPLES

Hereinafter, examples of the present invention will be described together with comparative examples. Incidentally, the present invention is not limited to the following examples.

Synthesis of Intermediate Compound

Synthetic Example 1: Synthesis of 2,4-diamino-6-(6-aminohexylamino)-1,3,5-triazine A reaction vessel (a four-necked flask equipped with a stirring blade, a thermometer and a reflux condenser) was charged with 380.4 parts by weight of hexamethylenediamine and 59.5 parts by weight of 2-chloro-4,6-diamino-1,3,5-triazine, the inside of the reaction vessel was purged with nitrogen gas, and the mixture was then heated to 110° C. over 1 hour, and then stirred for 3 hours. The reaction solution was concentrated under reduced pressure, and then dissolved in methanol, and filtration was performed, followed by purification by reprecipitation with tetrahydrofuran. Thereafter, the purified product was washed with 9% aqueous ammonia, and then dried under reduced pressure to obtain the following chemical compound (80.5 parts by weight, yield: 87.5%).

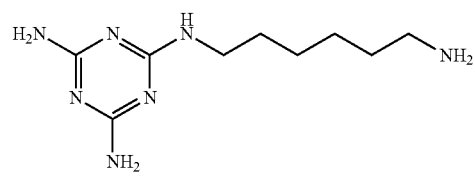 [SMILES: NCCCCCCNc1nc(N)nc(N)n1]

Synthesis Example 2: Synthesis of 2,4-diamino-6-(2-(2-aminoethyl sulfide)ethylamino)-1,3,5-triazine A reaction vessel was charged with 246.0 parts by weight of 2,2'-thiobis(ethylamine) and 119.0 parts by weight of 2-chloro-4,6-diamino-1,3,5-triazine, the inside of the reaction vessel was purged with nitrogen gas, and the mixture was then heated to 110° C. over 1 hour, and then stirred for 3 hours. The reaction solution was concentrated under reduced pressure, and then purified by silica gel column chromatography (developing solvent: methanol) to obtain the following chemical compound (82.8 parts by weight, yield: 44.2%).

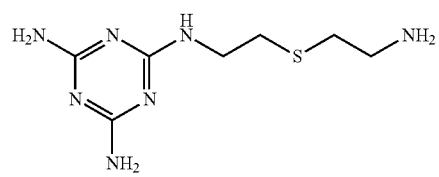

Synthesis Example 3: Synthesis of 2,4-diamino-6-(2-(2-(2-aminoethoxy)ethoxy)ethylamino)-1,3,5-triazine A reaction vessel was charged with 303.3 parts by weight of 1,2-bis(2-aminoethoxy)ethane and 119.0 parts by weight of 2-chloro-4,6-diamino-1,3,5-triazine, the inside of the reaction vessel was purged with nitrogen gas, and the mixture was then heated to 110° C. over 1 hour, and stirred for 3 hours. Thereafter, purification was performed in the same manner as in Synthesis Example 2 to obtain the following chemical compound (93.7 parts by weight, yield: 44.6%).

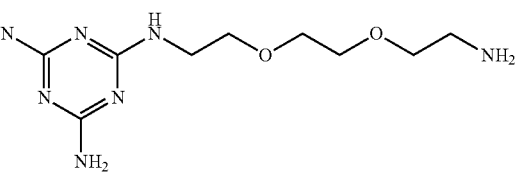

Synthetic Example 4: Synthesis of 2,4-diamino-6-(2-aminoethylamino)-1,3,5-triazine A reaction vessel was charged with 393.6 parts by weight of ethylenediamine and 59.5 parts by weight of 2-chloro-4,6-diamino-1,3,5-triazine, the inside of the reaction vessel was purged with nitrogen gas, and the mixture was then heated to 110° C. over 1 hour, and stirred for 3 hours. The reaction solution was concentrated under reduced pressure to distill off an excessive diamine, and then dissolved in 9% aqueous ammonia, and filtration was performed, followed by purification by reprecipitation with methanol and tetrahydrofuran. The filtrate was dried under reduced pressure to obtain the following chemical compound (62.9 parts by weight, yield: 91.0%).

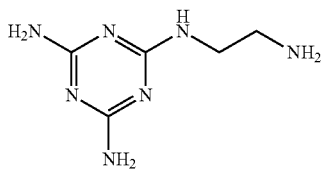 [SMILES: NCCNc1nc(N)nc(N)n1]

Synthesis Example 5: Synthesis of 2,4-diamino-6-(2-(2-aminoethylmethylamino)ethylamino)-1,3,5-triazine A reaction vessel was charged with 239.9 parts by weight of 2,2'-diamino-N-methyldiethylamine and 119 parts by weight of 2-chloro-4,6-diamino-1,3,5-triazine, the inside of the reaction vessel was purged with nitrogen gas, and the mixture was then heated to 110° C. over 1 hour, and stirred for 3 hours. Thereafter, purification was performed in the same manner as in Synthesis Example 2 to obtain the following chemical compound (81.5 parts by weight, yield: 44.1%).

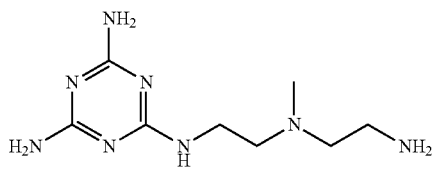 [SMILES: CN(CCN)CCNc1nc(N)nc(N)n1]

Synthesis Example 6: Synthesis of 2,4-dichloro-6-(3-(triethoxysilylpropyl)amino)-1,3,5-triazine The following chemical compound was synthesized in the manner described in the example section of WO 2013/186941.

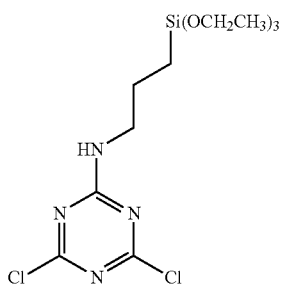

Synthesis Example 7: Synthesis of 2,4-dichloro-6-(3-(diethoxymethylsilyl)propyl)amino)-1,3,5-triazine The following chemical compound was synthesized in the manner described in the example section of WO 2013/186941.

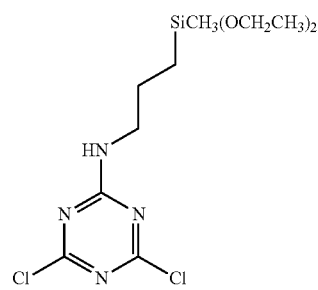

Synthesis Example 8: Synthesis of 2,4-dichloro-6-(bis(3-triethoxysilylpropyl)amino)-1,3,5-triazine The following chemical compound was synthesized in the manner described in the example section of WO 2013/186941.

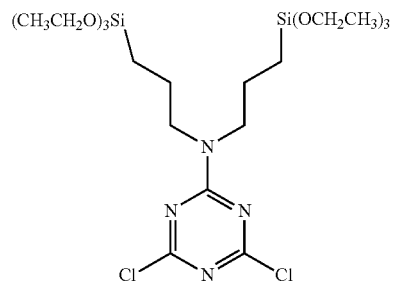

Synthesis Example 9: Synthesis of 2-chloro-4,6-bis(3-(triethoxysilylpropyl)amino)-1,3,5-triazine The following chemical compound was synthesized in the manner described in the example section of WO 2013/186941.

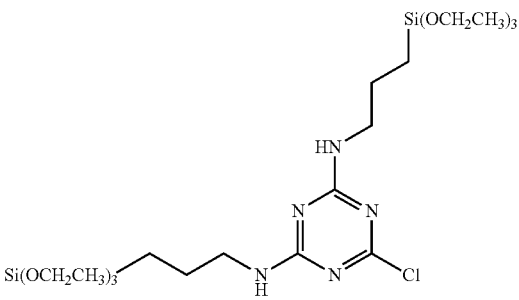

Synthesis Example 10: Synthesis of N,N-bis(4-(2-chloro-6-(3-triethoxysilylpropyl)amino-1,3,5-triazin)-yl)-ethylenediamine A four-necked flask equipped with a stirring blade, a thermometer and a dropping funnel was charged with 300 parts by weight of tetrahydrofuran and 191.3 parts by weight of 2,4-dichloro-6-(3-(triethoxysilylpropyl)amino)-1,3,5-triazine, and the inside of the reaction vessel was purged with nitrogen gas, followed by adjustment to 30° C. To the resulting solution, a mixture of 47.5 parts by weight of triethylamine, 14.1 parts by weight of ethylenediamine and 100 parts by weight of tetrahydrofuran was added dropwise over 2 hours, and the mixture was then stirred for 2 hours. The resulting liquid was cooled to 0° C., then left standing, subjected to decantation, and then filtered. The filtrate was concentrated with a rotary evaporator. Thereafter, purification by silica gel column chromatography (developing solvent: chloroform) was performed to obtain the following chemical compound (135.0 parts by weight, yield: 79%).

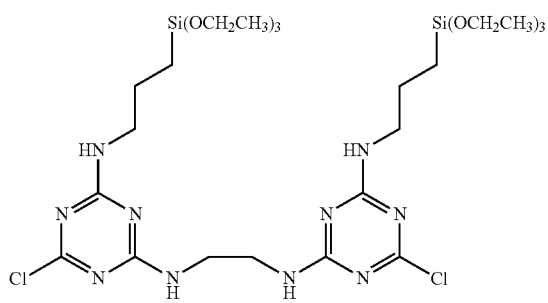

Synthesis of Chemical Compound for Surface Treating Agent

Chemical compounds shown in Tables 1 to 5 were synthesized in the manner described in synthesis examples below. Compounds 101, 102 and 103 were synthesized in the manner described in the example section WO 2013/186941. Commercially of available 3-(2-aminoethylamino)propyltrimethoxysilane was used as Compound 108.

The chemical compounds obtained by synthesis were each analyzed by liquid chromatography/mass spectrometry (LC/MS), and confirmed to be a desired chemical compound by detection of ions having a m/z value corresponding to a proton adduct of the desired chemical compound and a sodium adduction (see values of $[M+H]^+$ and $[M+Na]^+$ in Tables 1 to 5). In the syntheses of the intermediate compounds, the purified chemical compound was analyzed by LC/MS to confirm that a desired product was synthesized.

Synthesis Example 21: Synthesis of Compound 1A

A reaction vessel (a four-necked flask equipped with a stirring blade, a thermometer and a reflux condenser) was charged with 300 parts by weight of dimethyl sulfoxide and 80.5 parts by weight of 2,4-diamino-6-(6-aminohexylamino)-1,3,5-triazine, the inside of the reaction vessel was purged with nitrogen gas, and the mixture was then heated to 70° C. To the resulting solution, a mixture of 66.0 parts by weight of 2,4-dichloro-6-(3-(triethoxysilylpropyl)amino)-1,3,5-triazine and 50 parts by weight of tetrahydrofuran was added to this solution, and the mixture was then stirred at 120° C. for 2 hours. The reaction solution was cooled to 50° C., 39.8 parts by weight of triethylamine was then added, and the mixture was stirred for 30 minutes. Thereafter, 50 parts by weight of tetrahydrofuran was added, filtration was performed, and the filtrate was concentrated with a rotary evaporator, and dried under reduced pressure. To the product, dimethyl sulfoxide was added to obtain a solution containing Compound 1A in an amount of 15 wt %.

Synthesis Example 22: Synthesis of Compound 1B

A reaction vessel was charged with 300 parts by weight of dimethyl sulfoxide and 82.8 parts by weight of 2,4-diamino-6-(2-(2-aminoethyl sulfide)ethylamino)-1,3,5-triazine, the inside of the reaction vessel was purged with nitrogen gas, and the mixture was then heated to 70° C. To the resulting solution, a mixture of 66.7 parts by weight of 2,4-dichloro-6-(3-(triethoxysilylpropyl)amino)-1,3,5-triazine and 50 parts by weight of tetrahydrofuran was added to this solution, and the mixture was then stirred at 120° C. for 2 hours. The reaction solution was cooled to 50° C., 40.2 parts by weight of triethylamine was then added, and the mixture was stirred for 30 minutes. Thereafter, purification was performed in the same manner as in Synthesis Example 21 to obtain a solution containing Compound 1B in an amount of 18 wt %.

Synthesis Example 23: Synthesis of Compound 1C

A reaction vessel was charged with 300 parts by weight of dimethyl sulfoxide and 31.5 parts by weight of 2,4-diamino-6-(2-aminoethylamino)-1,3,5-triazine, the inside of the reaction vessel was purged with nitrogen gas, and the mixture was then heated to 70° C. To the resulting solution, a mixture of 103.0 parts by weight of 2-chloro-4,6-bis(3-(triethoxysilylpropyl)amino)-1,3,5-triazine and 50 parts by weight of tetrahydrofuran was added to this solution, and the mixture was then stirred at 120° C. for 2 hours. The reaction solution was cooled to 50° C., 20.7 parts by weight of triethylamine was then added, and the mixture was stirred for 30 minutes. Thereafter, purification was performed in the same manner as in Synthesis Example 21 to obtain a solution containing Compound 1C in an amount of 13 wt %.

Synthesis Example 24: Synthesis of Compound 1D

A reaction vessel was charged with 300 parts by weight of dimethyl sulfoxide and 62.9 parts by weight of 2,4-diamino-6-(2-aminoethylamino)-1,3,5-triazine, the inside of the reaction vessel was purged with nitrogen gas, and the mixture was then heated to 70° C. To the resulting solution, a mixture of 68.7 parts by weight of 2,4-dichloro-6-(3-(triethoxysilylpropyl)amino)-1,3,5-triazine and 50 parts by weight of tetrahydrofuran was added to this solution, and the mixture was then stirred at 120° C. for 2 hours. The reaction solution was cooled to 50° C., 41.4 parts by weight of triethylamine was then added, and the mixture was stirred for 30 minutes. Thereafter, purification was performed in the same manner as in Synthesis Example 21 to obtain a solution containing Compound 1D in an amount of 15 wt %.

Synthesis Example 25: Synthesis of Compound 1E

A reaction vessel was charged with 300 parts by weight of dimethyl sulfoxide and 62.9 parts by weight of 2,4-diamino-6-(2-aminoethylamino)-1,3,5-triazine, the inside of the reaction vessel was purged with nitrogen gas, and the mixture was then heated to 70° C. To the resulting solution, a mixture of 63.1 parts by weight of 2,4-dichloro-6-(3-(dietoxymethylsilylpropyl)amino)-1,3,5-triazine and 50 parts by weight of tetrahydrofuran was added to this solution, and the mixture was then stirred at 120° C. for 2 hours. The reaction solution was cooled to 50° C., 41.4 parts by weight of triethylamine was then added, and the mixture was stirred for 30 minutes. Thereafter, purification was performed in the same manner as in Synthesis Example 21 to obtain a solution containing Compound 1E in an amount of 16 wt %.

Synthesis Example 26: Synthesis of Compound 1F

A reaction vessel was charged with 300 parts by weight of dimethyl sulfoxide and 62.9 parts by weight of 2,4-diamino-6-(2-aminoethylamino)-1,3,5-triazine, the inside of the reaction vessel was purged with nitrogen gas, and the mixture was then heated to 70° C. To the resulting solution, a mixture of 60.9 parts by weight of 2,4-dichloro-6-(3-(trimethoxysilylpropyl)amino)-1,3,5-triazine and 50 parts by weight of tetrahydrofuran was added to this solution, and the mixture was then stirred at 120° C. for 2 hours. The reaction solution was cooled to 50° C., 41.4 parts by weight of triethylamine was then added, and the mixture was stirred for 30 minutes. Thereafter, purification was performed in the same manner as in Synthesis Example 21 to obtain a solution containing Compound 1F in an amount of 18 wt %.

Synthesis Example 27: Synthesis of Compound 1G

A reaction vessel was charged with 300 parts by weight of dimethyl sulfoxide and 93.7 parts by weight of 2,4-diamino-6-(2-(2-(2-aminoethoxy)ethoxy)ethylamino)-1,3,5-triazine, the inside of the reaction vessel was purged with nitrogen gas, and the mixture was then heated to 70° C. To the resulting solution, a mixture of 67.3 parts by weight of 2,4-dichloro-6-(3-(triethoxysilylpropyl)amino)-1,3,5-triazine and 50 parts by weight of tetrahydrofuran was added to this solution, and the mixture was then stirred at 120° C. for 2 hours. The reaction solution was cooled to 50° C., 40.5 parts by weight of triethylamine was then added, and the mixture was stirred for 30 minutes. Thereafter, purification was performed in the same manner as in Synthesis Example 21 to obtain a solution containing Compound 1G in an amount of 20 wt %.

Synthesis Example 28: Synthesis of Compound 1H

A reaction vessel was charged with 300 parts by weight of dimethyl sulfoxide and 62.9 parts by weight of 2,4-diamino-6-(2-aminoethylamino)-1,3,5-triazine, the inside of the reaction vessel was purged with nitrogen gas, and the mixture was then heated to 70° C. To the resulting solution, a mixture of 106.7 parts by weight of 2,4-dichloro-6-(bis(3-triethoxysilylpropyl)amino)-1,3,5-triazine and 50 parts by weight of tetrahydrofuran was added to this solution, and the mixture was then stirred at 120° C. for 2 hours. The reaction solution was cooled to 50° C., 41.4 parts by weight of triethylamine was then added, and the mixture was stirred for 30 minutes. Thereafter, purification was performed in the same manner as in Synthesis Example 21 to obtain a solution containing Compound 1H in an amount of 18 wt %.

Synthesis Example 29: Synthesis of Compound 1I

A reaction vessel was charged with 300 parts by weight of dimethyl sulfoxide and 62.9 parts by weight of 2,4-diamino-6-(2-aminoethylamino)-1,3,5-triazine, the inside of the reaction vessel was purged with nitrogen gas, and the mixture was then heated to 70° C. To the resulting solution, a mixture of 91.0 parts by weight of 2,4-dichloro-6-(bis(3-trimethoxysilylpropyl)amino)-1,3,5-triadine and 50 parts by weight of tetrahydrofuran was added to this solution, and the mixture was then stirred at 120° C. for 2 hours. The reaction solution was cooled to 50° C., 41.4 parts by weight of triethylamine was then added, and the mixture was stirred for 30 minutes. Thereafter, purification was performed in the same manner as in Synthesis Example 21 to obtain a solution containing Compound 1I in an amount of 15 wt %.

Synthesis Example 30: Synthesis of Compound 1J

A reaction vessel was charged with 300 parts by weight of dimethyl sulfoxide and 62.9 parts by weight of 2,4-diamino-6-(2-aminoethylamino)-1,3,5-triazine, the inside of the reaction vessel was purged with nitrogen gas, and the mixture was then heated to 70° C. To the resulting solution, a mixture of 135.0 parts by weight of N,N'-bis(4-(2-chloro-6-(3-triethoxysilylpropyl)amino-1,3,5-triazin)-yl)-ethylenediamine and 50 parts by weight of tetrahydrofuran was added to this solution, and the mixture was then stirred at 120° C. for 2 hours. The reaction solution was cooled to 50° C., 41.4 parts by weight of triethylamine was then added, and the mixture was stirred for 30 minutes. Thereafter, purification was performed in the same manner as in Synthesis Example 21 to obtain a solution containing Compound 1J in an amount of 19 wt %.

Synthesis Example 31: Synthesis of Compound 1K

A reaction vessel was charged with 300 parts by weight of dimethyl sulfoxide and 81.5 parts by weight of 2,4-diamino-6-(2-(2-aminoethylmethylamino)ethylamino)-1,3,5-triazine, the inside of the reaction vessel was purged with nitrogen gas, and the mixture was then heated to 70° C. To the resulting solution, a mixture of 66.5 parts by weight of 2,4-dichloro-6-(3-(triethoxysilylpropyl)amino)-1,3,5-triazine and 50 parts by weight of tetrahydrofuran was added to this solution, and the mixture was then stirred at 120° C. for 2 hours. The reaction solution was cooled to 50° C., 40.1 parts by weight of triethylamine was then added, and the mixture was stirred for 30 minutes. Thereafter, purification was performed in the same manner as in Synthesis Example 21 to obtain a solution containing Compound 1K in an amount of 18 wt %.

TABLE 1

| Compound | Molecular Weight | Exact Mass M | [M + H]+ | [M + Na]+ |
|---|---|---|---|---|
| 1A | 747.00 | 746.47 | 747.48 | 769.46 |
| 1B | 755.01 | 754.35 | 755.36 | 777.34 |
| 1C | 686.97 | 686.38 | 687.39 | 709.37 |
| 1D | 634.79 | 634.35 | 635.36 | 657.34 |

TABLE 1-continued

| Compound | Molecular Weight | Exact Mass M | [M + H]+ | [M + Na]+ |
|---|---|---|---|---|
| 1E (structure with Si(OCH₂CH₃)₃) | 604.76 | 604.34 | 605.35 | 627.33 |
| 1F (structure with Si(OCH₃)₃) | 592.71 | 592.30 | 593.31 | 615.29 |

TABLE 2

| Compound | Molecular Weight | Exact Mass M | [M + H]+ | [M + Na]+ |
|---|---|---|---|---|
| 1G (structure with Si(OCH₂CH₃)₃) | 811.00 | 810.45 | 811.46 | 833.44 |

TABLE 2-continued

| Compound | Molecular Weight | Exact Mass M | [M + H]⁺ | [M + Na]⁺ |
|---|---|---|---|---|
| 1H | 839.13 | 838.46 | 839.47 | 861.45 |
| 1I | 754.97 | 754.37 | 755.38 | 777.36 |
| 1J | 991.29 | 990.54 | 991.55 | 1013.53 |
| 1K | 748.98 | 748.46 | 749.47 | 771.45 |

Synthesis Example 41: Synthesis of Compound 2A

A reaction vessel was charged with 47.3 parts by weight of 3-(2-aminoethylamino)isobutyltrimethoxysilane, 72.8 parts by weight of 2-chloro-4,6-diamino-1,3,5-triazine and 200 parts by weight of dimethyl sulfoxide, and the mixture was stirred. To the resulting solution, 50.8 parts by weight of triethylamine and 20.0 parts by weight of methanol, the inside of the reaction vessel was purged with nitrogen gas, and the mixture was then heated to 95° C. over 1 hour, and then stirred for 6 hours. To the reaction solution was added 600 parts by weight of tetrahydrofuran, the mixture was cooled to room temperature, filtration was then performed, and the filtrate was concentrated with a rotary evaporator, and dried under reduced pressure. To the product, dimethyl sulfoxide was added to obtain a solution containing Compound 2A in an amount of 15 wt %.

Synthesis Example 42: Synthesis of Compound 2B

A reaction vessel was charged with 58.5 parts by weight of 8-(2-aminoethylamino)octyltrimethoxysilane, 72.8 parts by weight of 2-chloro-4,6-diamino-1,3,5-triazine and 200 parts by weight of dimethyl sulfoxide, and the mixture was stirred. To the resulting solution, 50.8 parts by weight of triethylamine and 20.0 parts by weight of methanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 2B in an amount of 18 wt %.

Synthesis Example 43: Synthesis of Compound 2C

A reaction vessel was charged with 44.5 parts by weight of 3-(2-aminoethylamino)propyltrimethoxysilane, 72.8 parts by weight of 2-chloro-4,6-diamino-1,3,5-triazine and 200 parts by weight of dimethyl sulfoxide, and the mixture was stirred. To the resulting solution, 50.8 parts by weight of triethylamine and 20.0 parts by weight of methanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 2C in an amount of 17 wt %.

Synthesis Example 44: Synthesis of Compound 2D

A reaction vessel was charged with 41.3 parts by weight of 3-(2-aminoethylamino)propyldimethoxymethylsilane, 72.8 parts by weight of 2-chloro-4,6-diamino-1,3,5-triazine and 200 parts by weight of dimethyl sulfoxide, and the mixture was stirred. To the resulting solution, 50.8 parts by weight of triethylamine and 20.0 parts by weight of methanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 2D in an amount of 18 wt %.

Synthesis Example 45: Synthesis of Compound 2E

A reaction vessel was charged with 62.5 parts by weight of (2-N-benzyl aminoethyl)-3-aminopropyl trimethoxysilane, 72.8 parts by weight of 2-chloro-4,6-diamino-1,3,5-triazine and 200 parts by weight of dimethyl sulfoxide, and the mixture was stirred. To the resulting solution, 50.8 parts by weight of triethylamine and 20.0 parts by weight of methanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 2E in an amount of 16 wt %.

Synthesis Example 46: Synthesis of Compound 2F

A reaction vessel was charged with 53.1 parts by weight of 3-[2-(2-aminoethylamino)ethylamino]propyltrimethoxysilane, 101.9 parts by weight of 2-chloro-4,6-diamino-1,3,5-triazine and 200 parts by weight of dimethyl sulfoxide, and the mixture was stirred. To the resulting solution, 71.0 parts by weight of triethylamine and 20.0 parts by weight of methanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 2F in an amount of 20 wt %.

Synthesis Example 47: Synthesis of Compound 2G

A reaction vessel was charged with 52.9 parts weight of 3-(2-aminoethylamino)propyltriethoxysilane, 72.8 parts by weight of 2-chloro-4,6-diamino-1,3,5-triazine and 200 parts by weight of dimethyl sulfoxide, and the mixture was stirred. To the resulting solution, 50.8 parts by weight of triethylamine and 20.0 parts by weight of ethanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 2G in an amount of 20 wt %.

Synthesis Example 48: Synthesis of Compound 2H

A reaction vessel was charged with 55.7 parts by weight of [3-(6-aminohexylamino)propyl]trimethoxysilane, 72.8 parts by weight of 2-chloro-4,6-diamino-1,3,5-triazine and 200 parts by weight of dimethyl sulfoxide, and the mixture was stirred. To the resulting solution, 50.8 parts by weight of triethylamine and 20.0 parts by weight of methanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 2H in an amount of 18 wt %.

Synthesis Example 49: Synthesis of Compound 2I

A reaction vessel was charged with 76.9 parts by weight of N,N'-bis[3-(trimethoxysilyl)propyl]ethane-1,2-diamine, 72.8 parts by weight of 2-chloro-4,6-diamino-1,3,5-triazine and 200 parts by weight of dimethyl sulfoxide, and the mixture was stirred. To the resulting solution, 50.8 parts by weight of triethylamine and 20.0 parts by weight of methanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 2I in an amount of 17 wt %.

TABLE 3
| Compound | | Molecular Weight | Exact Mass | | |
|---|---|---|---|---|---|
| | | | M | [M + H]+ | [M + Na]+ |
| 2A | 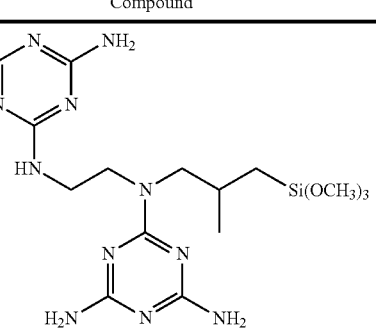 | 454.57 | 454.23 | 455.24 | 477.22 |
| 2B | 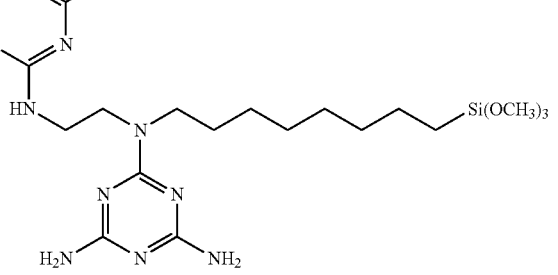 | 510.68 | 510.30 | 511.31 | 533.29 |
| 2C | 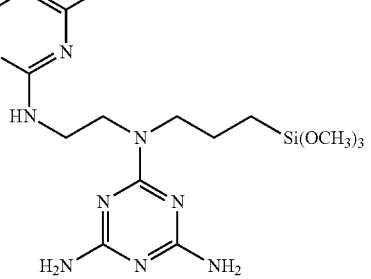 | 440.54 | 440.22 | 441.23 | 463.21 |
| 2D | 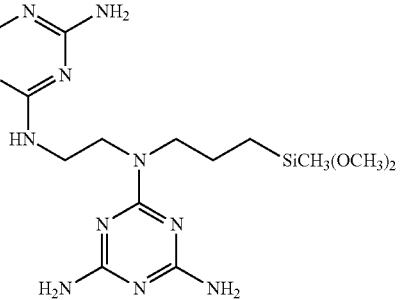 | 424.55 | 424.22 | 425.23 | 447.21 |
| 2E | 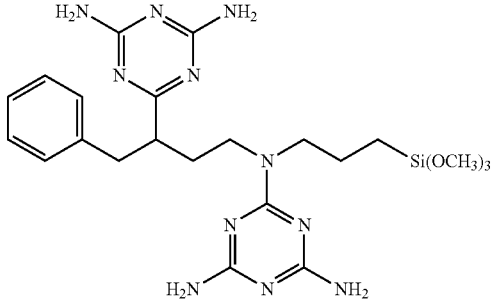 | 530.67 | 530.26 | 531.27 | 553.25 |

TABLE 3-continued
| Compound | | Molecular Weight | Exact Mass M | [M + H]+ | [M + Na]+ |
|---|---|---|---|---|---|
| 2F | 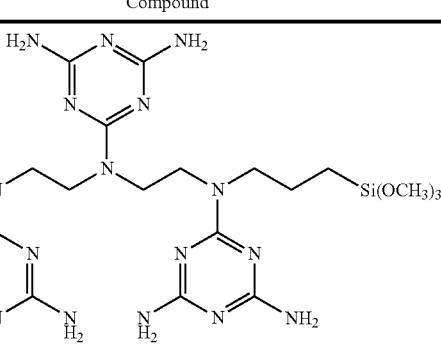 | 592.71 | 592.30 | 593.31 | 615.29 |
TABLE 4
| Compound | | Molecular Weight | Exact Mass M | [M + H]+ | [M + Na]+ |
|---|---|---|---|---|---|
| 2G | 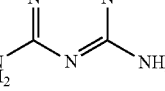 | 482.63 | 482.26 | 483.27 | 505.25 |
| 2H | 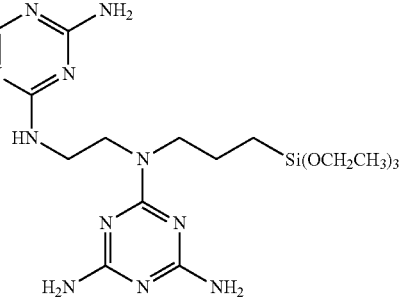 | 496.65 | 496.28 | 497.29 | 519.27 |
| 2I | 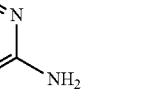 | 496.65 | 602.29 | 603.30 | 625.28 |

Synthesis Example 104: Synthesis of Compound 104

A reaction vessel was charged with 44.3 parts by weight of 3-aminopropyltriethoxysilane, 43.7 parts by weight of 2-chloro-4,6-diamino-1,3,5-triazine and 200 parts by weight of dimethyl sulfoxide, and the mixture was stirred. To the resulting solution, 30.6 parts by weight of triethylamine and 20.0 parts by weight of ethanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 104 in an amount of 16 wt %.

Synthesis Example 105: Synthesis of Compound 105

A reaction vessel was charged with 35.9 parts by weight of 3-aminopropyltriethoxysilane, 43.7 parts by weight of 2-chloro-4,6-diamino-1,3,5-triazine and 200 parts by weight of dimethyl sulfoxide, and the mixture was stirred. To the resulting solution, 30.6 parts by weight of triethylamine and 20.0 parts by weight of methanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 105 in an amount of 18 wt %.

Synthesis Example 106: Synthesis of Compound 106

A reaction vessel was charged with 38.7 parts by weight of N-methyl-3-(trimethoxysilyl) propylamine, 43.7 parts by weight of 2-chloro-4,6-diamino-1,3,5-triazine and 200 parts by weight of dimethyl sulfoxide, and the mixture was stirred. To the resulting solution, 30.6 parts by weight of triethylamine and 20.0 parts by weight of methanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 106 in an amount of 16 wt %.

Synthesis Example 107: Synthesis of Compound 107

A reaction vessel was charged with 47.1 parts by weight of [3-(butylamino)propyl]trimethoxysilane, 43.7 parts by weight of 2-chloro-4,6-diamino-1,3,5-triazine and 200 parts by weight of dimethyl sulfoxide, and the mixture was stirred. To the resulting solution, 30.6 parts by weight of triethylamine and 20.0 parts by weight of methanol, the inside of the reaction vessel was purged with nitrogen gas, and the mixture was then heated to 95° C. over 1 hour, and then stirred for 6 hours. Thereafter, purification was performed in the same manner as in Synthesis Example 41 to obtain a solution containing Compound 107 in an amount of 18 wt %.

TABLE 5

| Compound | | Molecular Weight | Exact Mass | | |
| --- | --- | --- | --- | --- | --- |
| | | | M | [M + H]$^+$ | [M + Na]$^+$ |
| 101 | Si(OCH$_2$CH$_3$)$_3$ structure | 416.60 | 416.27 | 417.28 | 439.26 |
| 102 | Si(OCH$_2$CH$_3$)$_3$ structure | 528.82 | 528.39 | 529.40 | 551.38 |

TABLE 5-continued

| Compound | | Molecular Weight | Exact Mass | | |
|---|---|---|---|---|---|
| | | | M | [M + H]+ | [M + Na]+ |
| 103 | (structure: bis-triazine with Si(OCH2CH3)3 groups, HN linkers, ethylene bridge, H2N and NH2 terminal groups) | 773.10 | 772.47 | 773.48 | 795.46 |
| 104 | H2N-triazine-NH-propyl-Si(OCH2CH3)3 (with H2N substituent) | 330.46 | 330.18 | 331.19 | 353.17 |
| 105 | H2N-triazine-NH-propyl-Si(OCH3)3 (with H2N substituent) | 288.38 | 288.14 | 289.15 | 311.13 |
| 106 | H2N-triazine-N(CH3)-propyl-Si(OCH3)3 (with H2N substituent) | 302.41 | 302.15 | 303.16 | 325.14 |
| 107 | H2N-triazine-N(butyl)-propyl-Si(OCH3)3 (with H2N substituent) | 344.49 | 344.20 | 345.21 | 367.19 |
| 108 | H2N-CH2CH2-NH-propyl-Si(OCH3)3 | 222.36 | 222.14 | 223.15 | 245.13 |

[Preparation of Surface Treating Agent]

The surface treating agents were dissolved in a solvent at concentrations shown in Tables 6 and 7, thereby preparing solutions (surface treating agents). As the solvent, dimethyl sulfoxide (DMSO), a mixed solvent of DMSO and methanol at 1:1, a mixed solvent of DMSO and ethanol at 1:1, or a mixed solvent of DMSO and ion-exchanged water (DIW) at 2:1 was used.

[Evaluation of Adhesiveness]

An electrolytic copper foil (3EC-III manufactured by Mitsui Mining & Smelting Co., Ltd., thickness: 35 μm) cut to 100 mm×100 mm was immersed and shaken in a 6.25 wt % sulfuric acid aqueous solution at normal temperature for 30 seconds to perform a derusting treatment, then rinsed with water, and dried to give a test copper foil (test piece).

A test piece was immersed while being shaken for 180 seconds in each of solutions (25° C.) shown in Tables 6 and 7, the test piece was then taken out from the solution, and dried at 60° C. On the surface-treated test piece, an epoxy resin-impregnated glass-fabric prepreg (FR-4 grade) was stacked and pressed to join the copper foil and the resin. A rectangular cut 10 mm in width and 60 mm in length was made in the copper foil from a side opposite to a resin-stacking surface of the test piece, and a copper foil on an outer periphery portion of the cut was peeled off. This sample was left standing for 50 hours under conditions of 130° C., a relative humidity of 85% and 2 atm to conduct and a high accelerates stress test (HAST). The tip of the copper foil of the sample after HAST was grasped with a gripper, and a 90° peeling test was conducted over a length of 60 mm at a peel rate of 50 mm/min in accordance with JIS C6481 to measure the peel strength.

Tables 6 and 7 show the formulations of solutions and the results of evaluation of adhesiveness in Examples and Comparative Examples.

TABLE 6

| | Compound | Concentration [mmol/L] | Solvent | Peel Strength [N/mm] |
|---|---|---|---|---|
| Example 1 | 1A | 20 | DMSO/Ethanol | 0.25 |
| Example 2 | 1A | 30 | DMSO | 0.26 |
| Example 3 | 1B | 20 | DMSO/DIW | 0.20 |
| Example 4 | 1B | 20 | DMSO/Ethanol | 0.21 |
| Example 5 | 1C | 20 | DMSO/Ethanol | 0.22 |
| Example 6 | 1D | 10 | DMSO | 0.27 |
| Example 7 | 1D | 10 | DMSO/DIW | 0.28 |
| Example 8 | 1D | 40 | DMSO/Ethanol | 0.30 |
| Example 9 | 1D | 50 | DMSO/DIW | 0.30 |
| Example 10 | 1D | 50 | DMSO | 0.28 |
| Example 11 | 1D | 150 | DMSO | 0.29 |
| Example 12 | 1E | 30 | DMSO | 0.25 |
| Example 13 | 1F | 50 | DMSO/DIW | 0.29 |
| Example 14 | 1F | 20 | DMSO | 0.27 |
| Example 15 | 1G | 20 | DMSO/Ethanol | 0.20 |
| Example 16 | 1G | 30 | DMSO | 0.21 |
| Example 17 | 1H | 40 | DMSO/Ethanol | 0.26 |
| Example 18 | 1I | 30 | DMSO | 0.26 |
| Example 19 | 1I | 40 | DMSO/DIW | 0.25 |
| Example 20 | 1J | 20 | DMSO/DIW | 0.27 |
| Example 21 | 1J | 30 | DMSO | 0.28 |
| Example 22 | 1K | 20 | DMSO/Ethanol | 0.20 |

TABLE 7

| | Compound | Concentration [mmol/L] | Solvent | Peel Strength [N/mm] |
|---|---|---|---|---|
| Example 41 | 2A | 30 | DMSO/Methanol | 0.20 |
| Example 42 | 2B | 30 | DMSO | 0.21 |
| Example 43 | 2C | 15 | DMSO | 0.28 |
| Example 44 | 2C | 15 | DMSO/DIW | 0.27 |
| Example 45 | 2C | 60 | DMSO/Methanol | 0.29 |
| Example 46 | 2C | 75 | DMSO | 0.28 |
| Example 47 | 2C | 75 | DMSO/DIW | 0.30 |
| Example 48 | 2C | 200 | DMSO | 0.27 |
| Example 49 | 2D | 40 | DMSO | 0.25 |
| Example 50 | 2E | 30 | DMSO/Methanol | 0.21 |
| Example 51 | 2F | 40 | DMSO/DIW | 0.27 |
| Example 52 | 2F | 20 | DMSO/Methanol | 0.30 |
| Example 53 | 2F | 60 | DMSO | 0.28 |
| Example 54 | 2G | 30 | DMSO/DIW | 0.29 |
| Example 55 | 2G | 40 | DMSO | 0.27 |
| Example 56 | 2H | 40 | DMSO | 0.22 |
| Example 57 | 2I | 30 | DMSO/DIW | 0.25 |
| Example 58 | 2I | 30 | DMSO/Methanol | 0.26 |
| Comparative Example 1 | 101 | 40 | DMSO/DIW | 0.04 |
| Comparative Example 2 | 101 | 50 | DMSO | 0.02 |
| Comparative Example 3 | 102 | 40 | DMSO | 0.03 |
| Comparative Example 4 | 103 | 20 | DMSO | 0.02 |
| Comparative Example 5 | 104 | 75 | DMSO | 0.07 |
| Comparative Example 6 | 105 | 60 | DMSO/DIW | 0.09 |
| Comparative Example 7 | 105 | 75 | DMSO | 0.08 |
| Comparative Example 8 | 106 | 40 | DMSO | 0.05 |
| Comparative Example 9 | 107 | 40 | DMSO | 0.06 |
| Comparative Example 10 | 108 | 75 | DMSO | 0.01 |

In each of Examples 1 to 22 and Examples 41 to 58 where the surface treatment was performed with a chemical compound containing two or more triazine rings and having —$NH_2$ directly bonded to the triazine ring, the peel strength was 0.20 N/mm or more, the coating film after the HAST test was hardly degraded, and excellent adhesiveness was exhibited.

In Comparative Example 10 where the copper foil was surface-treated with the Compound 108 which is a silane coupling agent free of a triazine ring, the peel strength of the sample was less than 0.1 N/mm in the high accelerated stress test, and the copper foil and the resin were not bonded to each other. In Comparative Examples 1 to 3 where the surface treatment was performed with the Compound 101 or 102 containing one triazine ring, the peel strength was less than 0.1 N/mm. In Comparative Example 4 using the Compound 103 which contains two triazine rings and two trialkoxysilyl groups and is free of —$NH_2$ directly bonded to a carbon atom of the triazine ring, the peel strength was less than 0.1 N/mm.

In Comparative Examples 5 to 9 where a copper foil was surface-treated with each of the Compounds 104 to 107 containing one triazine ring and having —$NH_2$ directly bonded to a carbon atom of the triazine ring, the peel strength of the sample in the high accelerated stress test was higher than that in each of Comparative Examples 1 to 4, but the peel strength was less than 0.10 N/mm, and the adhesiveness was not sufficient.

The invention claimed is:
1. A chemical compound represented by general formula (A):

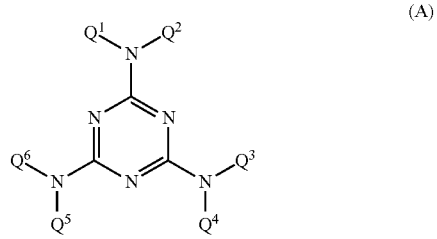

wherein $Q^1$ to $Q^6$ in the general formula (A) each independently represent a hydrogen atom, an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, X or Y,

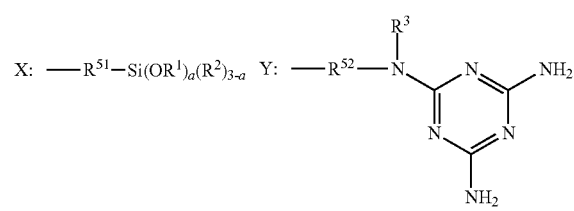

$R^{51}$ is an alkylene group having 1 to 12 carbon atoms and optionally containing a heteroatom, $R^{52}$ is an alkylene group having 1 to 12 carbon atoms and optionally containing a heteroatom; or a divalent organic group in which a main chain contains carbon and nitrogen atoms and the number of atoms forming the main chain is 20 or less and in which a part of the main chain forms a part of a 1,3,5-triazine ring, or a carbon atom of the 1,3,5-triazine ring is bonded to a nitrogen atom of the main chain, $R^1$ is a hydrogen atom or an alkyl group having 1 to 12 carbon atoms, $R^2$ is a hydrogen atom, or a monovalent hydrocarbon group selected from the group consisting of an alkyl group having 1 to 12 carbon atoms, an aryl group having 6 to 25 carbon atoms, and an aralkyl group having 7 to 30 carbon atoms, a is an integer of 1 to 3, $R^3$ is a hydrogen atom, or a monovalent organic group selected from the group consisting of an alkyl group having 1 to 12 carbon atoms, an aminoalkyl group having 1 to 12 carbon atoms, a substituted or unsubstituted aryl group having 6 to 25 carbon atoms, a substituted or unsubstituted aralkyl group having 7 to 30 carbon atoms, and X, and at least one of $Q^1$ to $Q^6$ is X and at least one of $Q^1$ to $Q^6$ is Y in the general formula (A).

2. The chemical compound of claim 1, wherein $Q^1$ is X, $Q^3$ is Y, and $Q^5$ is X, Y or a hydrogen atom in the general formula (A).

3. The chemical compound of claim 2, wherein $Q^5$ is X.

4. The chemical compound of claim 2, wherein $Q^5$ is Y.

5. The chemical compound of claim 2, wherein each of $Q^2$ and $Q^6$ is a hydrogen atom, and $Q^4$ is a hydrogen atom or X in the general formula (A).

6. The chemical compound of claim 1, wherein $Q^1$ is X, and $Q^2$ is Y in the general formula (A).

7. The chemical compound of claim 6, wherein each of $Q^3$, $Q^4$, $Q^5$ and $Q^6$ is a hydrogen atom in the general formula (A).

8. A surface treating agent, comprising: a chemical compound according to claim 1; and a solvent.

9. A surface treating method, comprising: bringing the surface treating agent of claim 8 into contact with a metal member to surface treat the metal member.

10. The surface treating method of claim 9, wherein the metal member is copper or copper alloy.

11. A production method for metal-resin composition, comprising: surface treating a metal member by the method of claim 9, and then joining a resin member onto the surface-treated metal member.

* * * * *